US012678625B2

(12) United States Patent
Single et al.

(10) Patent No.: US 12,678,625 B2
(45) Date of Patent: Jul. 14, 2026

(54) METHOD AND SYSTEM FOR ARTEFACT MITIGATION OF A NEURAL RESPONSE

(71) Applicant: Saluda Medical Pty Ltd, Level (AU)

(72) Inventors: Peter Scott Vallack Single, Artarmon (AU); Dean Michael Karantonis, Artarmon (AU); Daniel John Parker, Artarmon (AU); Samuel Nicholas Gilbert, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 470 days.

(21) Appl. No.: 18/314,717

(22) Filed: May 9, 2023

(65) Prior Publication Data

US 2023/0355984 A1     Nov. 9, 2023

(30) Foreign Application Priority Data

May 9, 2022     (AU) ................................. 2022901227

(51) Int. Cl.
| | |
|---|---|
| *A61N 1/36* | (2006.01) |
| *A61B 5/00* | (2006.01) |

(52) U.S. Cl.
CPC ........ *A61N 1/36139* (2013.01); *A61B 5/7203* (2013.01); *A61N 1/36125* (2013.01)

(58) Field of Classification Search
CPC ........... A61N 1/36139; A61N 1/36125; A61N 1/0551; A61N 1/36071; A61N 1/36062;
(Continued)

(56) References Cited

U.S. PATENT DOCUMENTS

| | | | |
|---|---|---|---|
| 5,792,212 | A | 8/1998 | Weijand et al. |
| 7,171,261 | B1 | 1/2007 | Litvak et al. |

(Continued)

FOREIGN PATENT DOCUMENTS

| | | |
|---|---|---|
| WO | 2012155183 A1 | 11/2012 |
| WO | 2012155188 A1 | 11/2012 |

(Continued)

OTHER PUBLICATIONS

Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
(Continued)

*Primary Examiner* — Carl H Layno
*Assistant Examiner* — Mary Grace Schlueter
(74) *Attorney, Agent, or Firm* — Barnes & Thornburg LLP

(57)     ABSTRACT
There is provided a method and implantable device for controlling a neural stimulus, the neural stimulus being defined by an artefact mitigation status. The method comprises generating a first neural stimulus for delivery to neural tissue, sensing a first signal subsequent to the first neural stimulus, generating a second neural stimulus for delivery to the neural tissue, and sensing a second signal subsequent to the second neural stimulus. The method further comprises determining an artefact mitigation measure (AMM) effect level based on the first sensed signal and the second sensed signal, and setting, in response to comparing the AMM effect level with an AMM effect threshold, the artefact mitigation status of a third neural stimulus to active.

40 Claims, 14 Drawing Sheets

(58) Field of Classification Search

CPC ..... A61B 5/7203; A61B 5/388; A61B 5/4836; A61B 5/686; A61B 5/24

USPC ........................................................ 607/62

See application file for complete search history.

(56) References Cited

U.S. PATENT DOCUMENTS

| | | | |
|---|---|---|---|
| 7,283,877 B1 | 10/2007 | Litvak et al. | |
| 7,447,549 B2 | 11/2008 | Litvak et al. | |
| 9,044,155 B2 | 6/2015 | Strahl | |
| 9,511,231 B1 | 12/2016 | Kent et al. | |
| 10,136,832 B2 | 11/2018 | Liu et al. | |
| 10,335,547 B2 | 7/2019 | Ward et al. | |
| 10,342,980 B2 | 7/2019 | Troosters et al. | |
| 10,842,996 B2 | 11/2020 | Baru et al. | |
| 10,980,487 B2 | 4/2021 | Markovic et al. | |
| 10,994,136 B2 | 5/2021 | Brill et al. | |
| 11,259,732 B2 | 3/2022 | Parramon et al. | |
| 11,350,882 B2 | 6/2022 | Baag et al. | |
| 11,491,326 B2 | 11/2022 | Dinsmoor et al. | |
| 11,510,628 B2 | 11/2022 | Bhadra et al. | |
| 11,559,258 B2 | 1/2023 | Dinsmoor et al. | |
| 11,596,797 B2 | 3/2023 | Sabes et al. | |
| 2010/0114200 A1* | 5/2010 | Krause | A61N 1/37 607/59 |
| 2017/0120058 A1* | 5/2017 | Ghosh | A61N 1/3956 |
| 2019/0366094 A1* | 12/2019 | Esteller | A61B 5/24 |
| 2020/0093437 A1 | 3/2020 | Melman et al. | |
| 2021/0052898 A1 | 2/2021 | Robinson et al. | |
| 2021/0138250 A1 | 5/2021 | Esteller et al. | |
| 2021/0267518 A1 | 9/2021 | Parker et al. | |
| 2022/0008726 A1 | 1/2022 | Corey et al. | |
| 2022/0008729 A1 | 1/2022 | Zhu | |
| 2022/0032065 A1 | 2/2022 | Stanslaski et al. | |
| 2022/0039724 A1 | 2/2022 | Parker et al. | |
| 2022/0062638 A1 | 3/2022 | Dinsmoor et al. | |
| 2022/0062639 A1 | 3/2022 | Dinsmoor et al. | |
| 2022/0072307 A1 | 3/2022 | Melman et al. | |
| 2022/0118251 A1 | 4/2022 | Buddha et al. | |
| 2022/0134110 A1 | 5/2022 | Esteller et al. | |
| 2022/0142539 A1 | 5/2022 | Wagenbach et al. | |
| 2022/0233866 A1 | 7/2022 | Gururaj et al. | |
| 2022/0248999 A1 | 8/2022 | Parker et al. | |
| 2022/0266022 A1 | 8/2022 | Steinke et al. | |
| 2022/0266027 A1 | 8/2022 | Zhang et al. | |
| 2022/0287646 A1* | 9/2022 | Sannelli | A61B 5/686 |
| 2022/0323764 A1 | 10/2022 | Esteller et al. | |
| 2022/0395690 A1 | 12/2022 | Haddock et al. | |
| 2022/0401737 A1 | 12/2022 | Dinsmoor | |
| 2023/0062062 A1 | 3/2023 | Litvak et al. | |
| 2023/0142761 A1 | 5/2023 | Dinsmoor et al. | |
| 2023/0144885 A1 | 5/2023 | Zhang et al. | |
| 2023/0149716 A1 | 5/2023 | Hincapie Ordonez et al. | |

FOREIGN PATENT DOCUMENTS

| | | | | | |
|---|---|---|---|---|---|
| WO | 2014071445 A1 | 5/2014 | | | |
| WO | 2015074121 A1 | 5/2015 | | | |
| WO | 2015168735 A1 | 11/2015 | | | |
| WO | WO-2020082126 A1 * | 4/2020 | ......... | A61N 1/36139 | |
| WO | 2020124135 A1 | 6/2020 | | | |
| WO | 2021232091 A1 | 11/2021 | | | |
| WO | 2022040753 A1 | 3/2022 | | | |
| WO | 2022040754 A1 | 3/2022 | | | |
| WO | WO-2022150638 A1 * | 7/2022 | ......... | A61N 1/36146 | |
| WO | 2022182611 A1 | 9/2022 | | | |
| WO | 2022183163 A1 | 9/2022 | | | |
| WO | 2022197748 A1 | 9/2022 | | | |
| WO | 2022217322 A1 | 10/2022 | | | |
| WO | 2023020544 A1 | 2/2023 | | | |
| WO | 2023031740 A1 | 3/2023 | | | |
| WO | 2023087053 A1 | 5/2023 | | | |

OTHER PUBLICATIONS

Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.

Bahmer et al., "Effects of electrical pulse polarity shape on intra cochlear neural responses in humans: Triphasic pulses with cathodic second phase", Hearing Research, 2013, vol. 306, pp. 123-130.

Blum, "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.

Chakravarthy et al., "A Clinical Feasibility Study of Spinal Evoked Compound Action Potential Estimation Methods", Neuromodulation 2022; 25:75-84.

Dillier et al., "Measurement of the electrically evoked compound action potential via a neural response telemetry system", Ann. Otol. Rhinol. Laryngol., May 2002, vol. 111, No. 5, pp. 407-414.

Gnadt et al., "Spectral Cancellation of Microstimulation Artifact for Simultaneous Neural Recording in Situ", IEEE Transactions on Biomedical Engineering, Oct. 2003, Date of Publication: Sep. 23, 2003, vol. 50, No. 10, pp. 1129-1135, DOI: 10.1109/TBME.2003. 816077.

Kent, "Characterization of Evoked Potentials During Deep Brain Stimulation in the Thalamus", Dissertation, Duke University, 2013, Retrieved from https://hdl.handle.net/10161/8195. https://dukespace. lib.duke.edu/dspace/handle/10161/8195.

Kent et al., "Recording evoked potentials during deep brain stimulation: development and validation of instrumentation to suppress the stimulus artefact", J Neural Eng., Jun. 2012, vol. 9, No. 3, 036004, doi: 10.1088/1741 2560/9/3/036004.

Kim et al., "A Wavelet-Based Method for Action Potential Detection From Extracellular Neural Signal Recording With Low Signal-to-Noise Ratio", IEEE Transactions on Biomedical Engineering, Aug. 2003, vol. 50. No. 8, pp. 999-1011.

Madhukar et al., "Modelling of compound nerve action potentials health and disease", Engineering in Medicine and Biology Society, 1992 14th Annual International Conference of the IEEE. vol. 6. IEEE, 1992. pp. 2600-2601.

Parker et al., "Electrically evoked compound action potential recording in peripheral nerves", Bioeletron. Med., vol. 1, No. 1, 2018, pp. 71-83, ISSN 2059-1500.

Scott et al, "Compact Nonlinear Model of an Implantable Electrode Array for Spinal Cord Stimulation (SCS)", IEEE Transactions on Biomedical Circuits and Systems, 2014, vol. 8, No. 3, pp. 382-390.

Shepherd et al., "Electrical stimulation of the auditory nerve: II. Effect of stimulus waveshape on single fibre response properties", Hearing Research, 1999, 130, 171-188.

Stanslaski et al., "Design and Validation of a Fully Implantable, Chronic, Closed-Loop Neuromodulation Device with Concurrent Sensing and Stimulation", IEEE Transactions on Neural Systems and Rehabilitation Engineering, Jul. 2012, Date of Publication: Jan. 23, 2012, vol. 20, No. 4, pp. 410-421, DOI: 10.1109/TNSRE.2012. 2183617.

Yuan et al., "Recording monophasic action potentials using a platinum-electrode ablation catheter", Europace. Oct. 2000; 2(4):312-319.

* cited by examiner

108

190

192

1340

150

100

110

190

METHOD AND SYSTEM FOR ARTEFACT MITIGATION OF A NEURAL RESPONSE

The present application claims priority from Australian Provisional Patent Application No 2022901227 filed on May 9, 2022, the contents of which are incorporated herein by reference in their entirety.

TECHNICAL FIELD

The present invention relates to the mitigation of artefacts associated with the measurement of compound action potentials evoked by neural stimulation. In particular, the invention relates to the determination of an indication to activate artefact mitigation measures.

BACKGROUND OF THE INVENTION

There is a range of situations in which it may be desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is positioned adjacent the target neural fibre(s) in the spinal cord, typically in the dorsal epidural space above the dorsal column. An electrical pulse of sufficient intensity applied to the target neural fibres by a stimulus electrode causes depolarisation of neurons in the fibres, which in turn generates an action potential in the fibres. Action potentials propagate along the fibres in orthodromic (in afferent fibres this means towards the head, or rostral) and antidromic (in afferent fibres this means towards the cauda, or caudal) directions. Action potentials propagating along Aβ (A-beta) fibres being stimulated in this way inhibit the transmission of pain from a region of the body innervated by the target neural fibres (the dermatome) to the brain. To sustain the pain relief effects, stimuli may be applied repeatedly, for example at a frequency in the range of 30 Hz-100 Hz.

For effective and comfortable neuromodulation, it may be desirable to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it may therefore be desirable to apply stimuli with intensity below a discomfort threshold, above which uncomfortable or painful percepts arise due to over-recruitment of Aβ fibres. (The discomfort threshold may alternatively be referred to as a 'comfort threshold'). When recruitment is too large, Aβ fibres produce uncomfortable sensations. Stimulation at high intensity may even recruit Aδ (A-delta) fibres, which are sensory nerve fibres associated with acute pain, cold and heat sensation. It may therefore be desirable to maintain stimulus intensity within a therapeutic range between the recruitment threshold and the discomfort threshold.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood to mean that the element may be any one of the listed options, or may be any combination of two or more of the listed options.

SUMMARY OF THE INVENTION

Disclosed herein is technology directed to the mitigation of artefacts associated with the measurement of compound action potentials evoked by neural stimulation. In particular, the present technology is directed to the determining whether to activate artefact mitigation measures.

According to one aspect of the present technology, there is provided a method of controlling a neural stimulus, the neural stimulus being defined by an artefact mitigation status. The method comprising generating a first neural stimulus for delivery to neural tissue, sensing a first signal subsequent to the first neural stimulus, generating a second neural stimulus for delivery to the neural tissue, and sensing a second signal subsequent to the second neural stimulus. The method further comprises determining an artefact mitigation measure (AMM) effect level based on the first sensed signal and the second sensed signal, and setting, in response to comparing the AMM effect level with an AMM effect threshold, the artefact mitigation status of a third neural stimulus to active. In one embodiment, the method further comprises generating the third neural stimulus for delivery to the neural tissue according to the artefact mitigation status.

In one embodiment, the artefact mitigation status of the first neural stimulus is active, and the artefact mitigation status of the second neural stimulus is inactive.

In one embodiment, the first neural stimulus is generated at supra-threshold intensity and the second neural stimulus is generated at supra-threshold intensity. In one embodiment, the method further comprises repeating the generating a first neural stimulus and the sensing a first signal to generate a plurality of first signals before determining the AMM effect level. In one embodiment, the method further comprises repeating the generating a second neural stimulus and the sensing a second signal to generate a plurality of second signals before determining the AMM effect level.

In one embodiment, determining the AMM effect level comprises determining an artefact-to-ECAP ratio of the first sensed signal, determining an artefact-to-ECAP ratio of the second sensed signal, and comparing the artefact-to-ECAP ratio of the first sensed signal to the artefact-to-ECAP ratio of the second sensed signal. In one embodiment, determining the artefact-to-ECAP ratio of the first sensed signal comprises applying basis element signal separation to the first sensed signal. In one embodiment, determining the artefact-to-ECAP ratio of the first sensed signal comprises fitting a growth curve model to the first sensed signal. In one embodiment, determining an artefact-to-ECAP ratio of the first sensed signal comprises fitting an artefact-aware growth curve model to the first sensed signal.

In one embodiment, the first neural stimulus is generated at sub-threshold intensity, and the second neural stimulus is generated at sub-threshold intensity.

In one embodiment, the first neural stimulus is defined by a first stimulus electrode configuration defining a first subset of stimulus electrodes from a plurality of stimulus electrodes of an electrode array, and the second neural stimulus is defined by a second stimulus electrode configuration defining a second subset of stimulus electrodes from the plurality of stimulus electrodes of the electrode array, the first subset differing from the second subset.

In one embodiment, the method further comprises, in response to the artefact mitigation status being active, controlling an electrical condition of the neural tissue. In one embodiment, controlling an electrical condition of the neural tissue comprises providing a plurality of electrodes including at least one nominal feedback sense electrode and at least one nominal compensation electrode, the electrodes being positioned proximate to the neural tissue and being in electrical contact with the neural tissue, connecting a feedback signal from the feedback sense electrode to an input of a feedback amplifier, and referencing the amplifier to a desired electrical value, and connecting an output of the feedback amplifier to the compensation electrode such that the feedback amplifier drives the neural tissue via the compensation electrode in a feedback arrangement which seeks to drive the feedback signal to the desired electrical value. In one embodiment, the desired electrical value is electrical ground referenced to a patient ground electrode distant from the feedback sense electrode.

According to another aspect of the present technology, there is provided an implantable device for controllably generating a neural stimulus, the neural stimulus being defined by an artefact mitigation activation status. The device comprises a stimulus source configured to generate neural stimuli to be delivered via one or more stimulus electrodes of an electrode array to neural tissue, measurement circuitry configured to sense signals of the neural tissue via one or more measurement electrodes of the electrode array subsequent to respective neural stimuli; and a controller. The controller is configured to control the stimulus source to generate a first neural stimulus for delivery to the neural tissue, sense, by the measurement circuitry, a first sensed signal of the tissue, subsequent to the first neural stimulus, and control the stimulus source to generate a second neural stimulus for delivery to the neural tissue. The controller is further configured to sense, by the measurement circuitry, a second sensed signal of the tissue, subsequent to the second neural stimulus, and determine an AMM effect level based on the first sensed signal and the second sensed signal. The controller is further configured to set, in response to comparing the AMM effect level with an AMM effect threshold, the artefact mitigation status of a third neural stimulus to active. In one embodiment, the controller is further configured to control the stimulus source to generate the third neural stimulus for delivery to the neural tissue according to the artefact mitigation status.

In one embodiment, the device further comprises the electrode array. The electrode array comprises a plurality of electrodes including the one or more stimulus electrodes and the one or more measurement electrodes.

In one embodiment, the artefact mitigation status is defined by an artefact mitigation configuration setting of the implantable device. In one embodiment, the controller is configured to, in response to the AMM effect level exceeding the AMM effect threshold, set the artefact mitigation status to active.

According to another aspect of the present technology, there is provided a neuromodulation system comprising an implantable device for controllably generating a neural stimulus, the neural stimulus being defined by an artefact mitigation activation status. The device comprises a stimulus source configured to generate neural stimuli to be delivered via one or more stimulus electrodes of an electrode array to neural tissue, measurement circuitry configured to sense signals of the neural tissue via one or more measurement electrodes of the electrode array subsequent to respective neural stimuli and a controller. The controller is configured to control the stimulus source to generate the neural stimuli. The neuromodulation system further comprises a processor. The processor is configured to instruct the controller to control the stimulus source to generate a first neural stimulus for delivery to the neural tissue and instruct the measurement circuitry to sense a first sensed signal of the neural tissue, subsequent to the first neural stimulus. The processor is also configured to instruct the controller to control the stimulus source to generate a second neural stimulus for delivery to the neural tissue and instruct the measurement circuitry to sense a second sensed signal of the neural tissue, subsequent to the second neural stimulus. The processor is further configured to determine an AMM effect level based on the first sensed signal and the second sensed signal. In response to comparing the AMM effect level with an AMM effect threshold, the processor is configured to set the artefact mitigation status to active.

In one embodiment, the neuromodulation system further comprises the electrode array, the electrode array comprising a plurality of electrodes including the one or more stimulus electrodes and the one or more measurement electrodes. In one embodiment, the artefact mitigation status is defined by an artefact mitigation configuration setting of the implantable device.

In one embodiment, in response to the AMM effect level exceeding the AMM effect threshold, the processor is configured to set the artefact mitigation status to active. In one embodiment, the processor is part of the implantable device. In one embodiment, the neuromodulation system further comprises an external computing device in communication with the implantable device. In one embodiment, the processor is part of the external computing device.

According to another aspect of the present technology, there is provided a method of controlling a neural stimulus, the neural stimulus being defined by an artefact mitigation status. The method comprises determining an impedance of a recording electrode, determining an impedance of a reference electrode, determining an expected artefact level based on the impedance of the recording electrode and the impedance of the reference electrode, and setting, in response to comparing the expected artefact level with a threshold artefact level, the artefact mitigation status of a neural stimulus to active. In one embodiment, the method further comprises generating the neural stimulus for delivery to a neural tissue according to the artefact mitigation status.

In one embodiment, the expected artefact level comprises an expected artefact magnitude. In one embodiment, the expected artefact level comprises an impedance difference between the impedance of the recording electrode and the impedance of the reference electrode. In one embodiment, the threshold artefact level comprises a threshold impedance difference. In one embodiment, determining the expected artefact level is further based on an input capacitance of an amplifier to which the recording electrode and the reference electrode are connected. In one embodiment, the threshold artefact level comprises a threshold artefact magnitude.

According to another aspect of the present technology, there is provided an implantable device for controllably generating a neural stimulus, the neural stimulus being defined by an artefact mitigation activation status. The device comprises a stimulus source configured to generate neural stimuli to be delivered via one or more stimulus electrodes of an electrode array to a neural tissue, measurement circuitry configured to sense signals of the neural tissue via one or more measurement electrodes of the electrode array subsequent to respective neural stimuli, and a controller. The controller is configured to determine an impedance of a recording electrode of the one or more measurement electrodes, determine an impedance of a reference electrode of the one or more measurement electrodes, determine an expected artefact level based on the impedance of the recording electrode and the impedance of the reference electrode, and set in response to comparing the expected artefact level with a threshold artefact level, the artefact mitigation status of a neural stimulus to active. In one embodiment, the controller is further configured to control the stimulus source to generate a neural stimulus for delivery to the neural tissue according to the artefact mitigation status.

According to another aspect of the present technology, there is provided a neuromodulation system comprising an implantable device for controllably generating a neural stimulus, the neural stimulus being defined by an artefact mitigation activation status. The device comprises a stimulus source configured to generate neural stimuli to be delivered via one or more stimulus electrodes of an electrode array to neural tissue, a measurement circuitry configured to sense signals of the neural tissue via one or more measurement electrodes of the electrode array subsequent to respective neural stimuli, and a controller configured to control the stimulus source to generate the neural stimuli. The device further comprises a processor configured to determine an impedance of a recording electrode of the one or more measurement electrodes, an impedance of a reference electrode of the one or more measurement electrodes and an expected artefact level based on the impedance of the recording electrode and the impedance of the reference electrode. In response to comparing the expected artefact level with a threshold artefact level, the processor is configured to set the artefact mitigation status of a neural stimulus to active. In one embodiment, the controller of the neuromodulation system is further configured to control the stimulus source to generate a neural stimulus for delivery to the neural tissue according to the artefact mitigation status. In one embodiment, the processor of the neuromodulation system is part of the implantable device. In one embodiment, the neuromodulation system further comprises an external computing device in communication with the implantable device. In one embodiment, the processor of the neuromodulation system is part of the external computing device.

BRIEF DESCRIPTION OF THE DRAWINGS

One or more implementations of the invention will now be described with reference to the accompanying drawings, in which.

DETAILED DESCRIPTION

Figure 1:
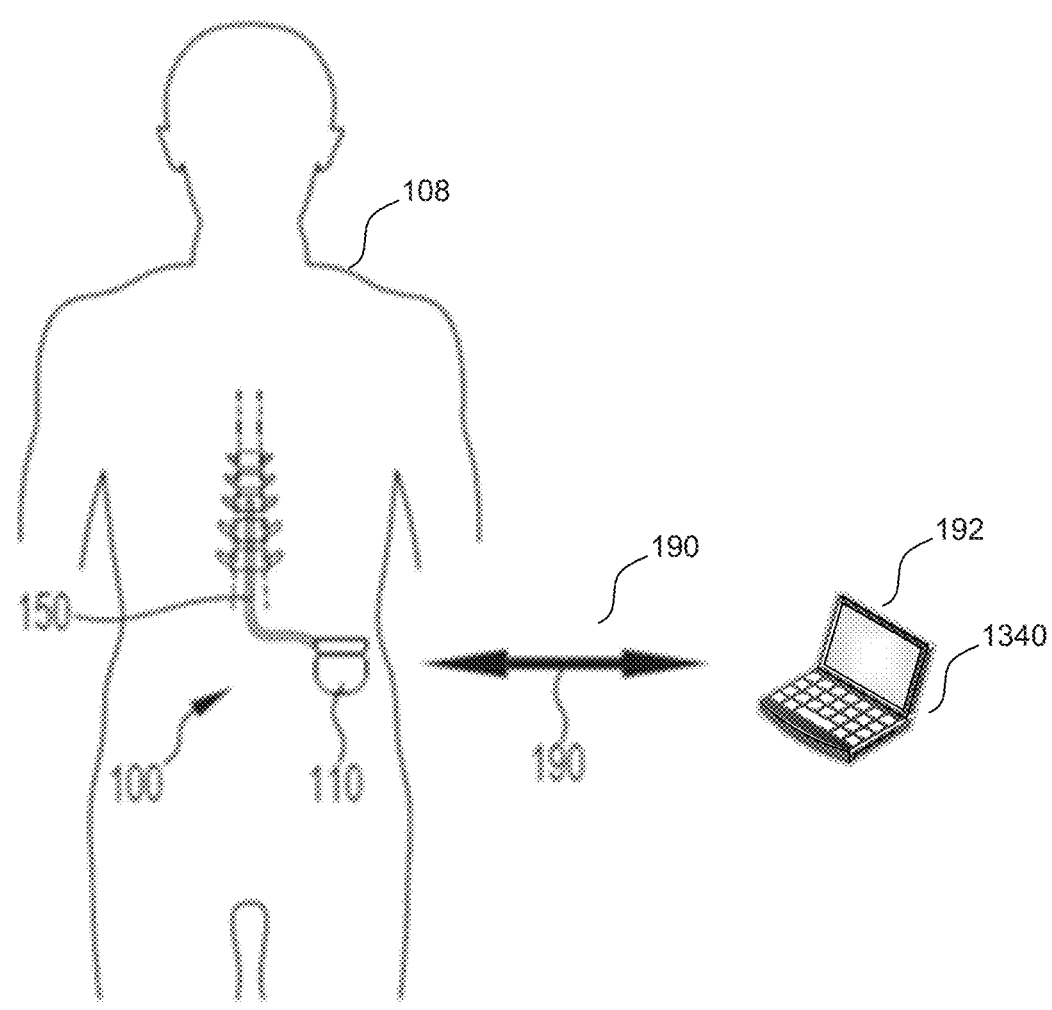
FIG. 1 schematically illustrates an implanted spinal cord stimulator, according to one implementation of the present technology.

The task of maintaining neural recruitment at a therapeutic level may be made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO2012/155188 by the present applicant, the contents of which are incorporated herein by reference. Feedback control seeks to compensate for relative nerve/electrode movement by controlling the intensity of the delivered stimuli to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range. It may therefore be desirable to accurately measure the intensity and other characteristics of a neural response evoked by the stimulus.

The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO2012/155183, the contents of which are incorporated herein by reference. Neural response measurement can be a difficult task as a neural response component in the sensed signal will typically have a maximum amplitude in the range of microvolts. In contrast, a stimulus applied to evoke the response is typically several volts, and manifests in the sensed signal response as crosstalk of that magnitude. Moreover, stimulus generally results in electrode artefact, which manifests in the sensed signal as a decaying output of the order of several millivolts after the end of the stimulus. As the neural response can be contemporaneous with the stimulus crosstalk and/or the stimulus artefact, neural response measurements present a difficult challenge of measurement amplifier design. For example, to resolve a 10 μV ECAP with 1 μV resolution in the presence of stimulus crosstalk of 5 V requires an amplifier with a dynamic range of 134 dB, which is impractical in implantable devices. In practice, many non-ideal aspects of a circuit lead to artefact, and as these aspects mostly result a time-decaying artefact waveform of positive or negative polarity, their identification and elimination can be laborious.

Evoked neural responses are less difficult to measure when they appear later in time than the artefact, or when the signal-to-noise ratio is sufficiently high. The artefact is often restricted to a time of 1-2 ms after the stimulus and so, provided the neural response is measured after this time window, a neural response measurement can be more easily obtained. This is the case in surgical monitoring where there are large distances (e.g. more than 12 cm for nerves conducting at 60 ms-1) between the stimulating and measurement electrodes so that the propagation time from the stimulus site to the measurement electrodes exceeds 2 ms, which is longer than the typical duration of stimulus artefact.

To characterize the responses from the dorsal column, high stimulation currents are required. Similarly, any implanted neuromodulation device will necessarily be of compact size, so that for such devices to monitor the effect of applied stimuli, the stimulus electrode(s) and measurement electrode(s) will necessarily be in close proximity. In such situations, the stimulus and measurement process must address the artefact directly.

FIG. 1—Implanted Spinal Cord Stimulator

FIG. 1 schematically illustrates an implanted spinal cord stimulator 100 in a patient 108, in accordance with an embodiment. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as in a flank or sub-clavicularly. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external computing device 192 via a transcutaneous communications channel 190. Communications channel 190 may be active on a substantially continuous basis, at periodic intervals, at non-periodic intervals, or upon request from the external computing device 192. External computing device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
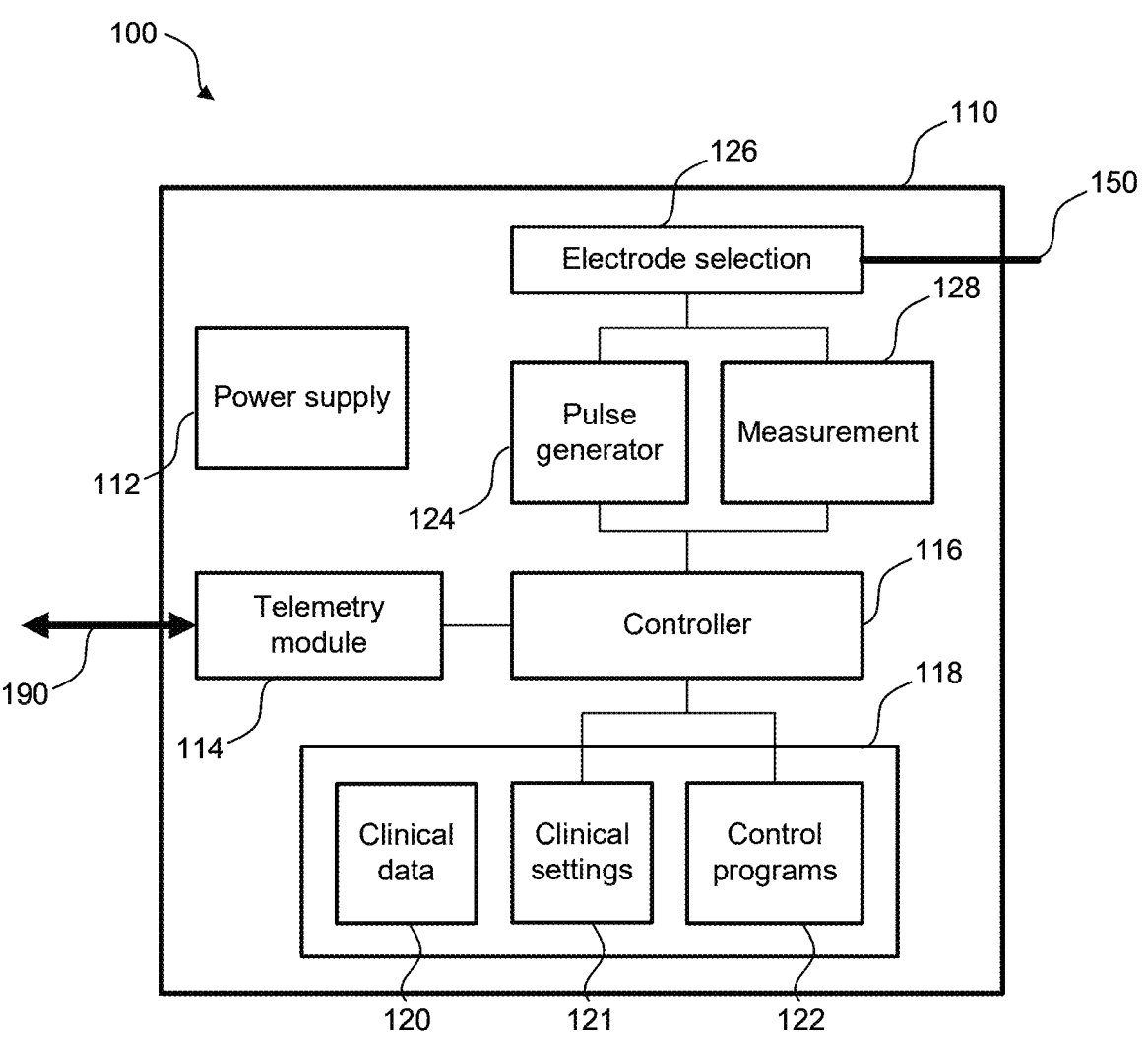
FIG. 2 is a block diagram of the stimulator of FIG. 1, in accordance with an embodiment.

FIG. 2—Block Diagram

FIG. 2 is a block diagram of the stimulator 100 of FIG. 1, in accordance with an embodiment. Electronics module 110 contains a battery 112 and a telemetry module 114. In implementations of the present technology, any suitable type of transcutaneous communications channel 190, such as infrared (IR), radiofrequency (RF), capacitive and inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 controls a pulse generator 124 to generate stimuli, such as in the form of electrical pulses, in accordance with the clinical settings 121 and control programs 122. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process measurements of neural responses sensed at measurement electrode(s) of the electrode array 150 as selected by electrode selection module 126.

Figure 3:
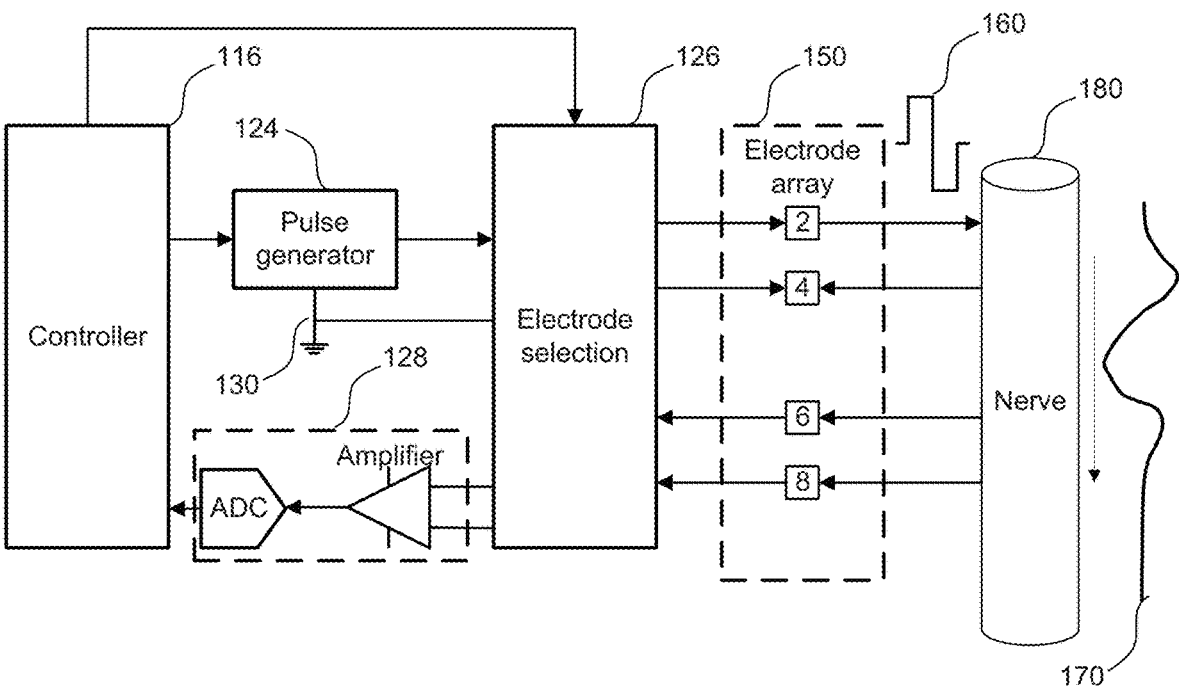
FIG. 3 schematically illustrates the interaction of an implanted stimulator with a nerve in a patient, in accordance with an embodiment.

FIG. 3—Interaction with Nerve

FIG. 3 is a schematic illustrating interaction of the implanted stimulator 100 with a nerve 180 in the patient 108, in accordance with an embodiment. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. Electrode selection module 126 also selects a return electrode 4 of the electrode array 150 for stimulus current return in each phase, to maintain a zero net charge transfer. An electrode may act as both a stimulus electrode and a return electrode over a complete multiphasic stimulus pulse. The use of two electrodes in this manner for delivering and returning current in each stimulus phase is referred to as bipolar stimulation. Alternative embodiments may apply other forms of bipolar stimulation, or may use a greater number of stimulus and/or return electrodes. The electrodes that the electrode section module 126 configures to act as stimulus and return electrodes are collectively called a stimulus electrode configuration (SEC).

Electrode selection module 126 is illustrated as connecting to a ground 130 of the pulse generator 124 to enable stimulus current return via the return electrode 4. However, other connections for current return may be used in other implementations.

Delivery of an appropriate stimulus via stimulus electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To "fit" the stimulator 100 to the patient 108, a clinician may cause the stimulator 100 to deliver stimuli of various configurations which seek to produce a sensation that is experienced by the user as paraesthesia. When a stimulus electrode configuration is found which evokes paraesthesia in a location and of a size which is congruent with the area of the patient's body affected by pain and of a quality that is comfortable for the patient, the clinician or the patient nominates that configuration for ongoing use. The therapy parameters may be loaded into the memory 118 of the stimulator 100 as the clinical settings 121.

The stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8. The electrode selection module 126 selectively connects the chosen electrodes to the inputs of the measurement circuitry 128. The electrodes that the electrode selection module 126 configures to act as measurement electrodes are collectively called a measurement electrode configuration (MEC). In one embodiment, the measurement electrode configuration (MEC) comprises two electrodes for differential ECAP recording.

Neural signals sensed by the measurement electrodes 6 and 8 subsequent to respective stimuli are passed to the measurement circuitry 128, which may comprise an amplifier and an analog-to-digital converter (ADC). The measurement electrode connected to the positive terminal of the measurement amplifier 129, via the electrode selection module 126, is referred to as the recording electrode, while the measurement electrode connected to the negative terminal of the measurement amplifier 129, via the electrode selection module 126, is referred to as the reference electrode. The measurement circuitry 128 for example may operate in accordance with the teachings of the above-mentioned International Patent Publication No. WO2012/155183.

Neural signals sensed by the measurement electrodes 6, 8 and processed by measurement circuitry 128 are analysed by an ECAP detector implemented within controller 116, configured by control programs 122, to obtain information regarding the effect of the applied stimulus upon the nerve 180. In some implementations, neural signals are analysed by the ECAP detector in a manner which measures one or more characteristics from each neural response or group of neural responses contained in the neural signals. In one such implementation, the characteristics comprise a peak-to-peak ECAP amplitude in microvolts (μV). For example, the sensed signals may be analysed by the ECAP detector to determine the peak-to-peak ECAP amplitude in accordance with the teachings of International Patent Publication No. WO2015/074121, the contents of which are incorporated herein by reference. Alternative implementations of the ECAP detector may measure an alternative characteristic from the neural response, or may measure and store two or more characteristics from the neural response.

Stimulator 100 applies stimuli over a potentially long period such as days, weeks, or months and during this time may store characteristics of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more characteristics such as a measure of the intensity of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external computing device 192, which may occur only once or twice a day, or less.

FIG. 4—ECAP

Figure 4:
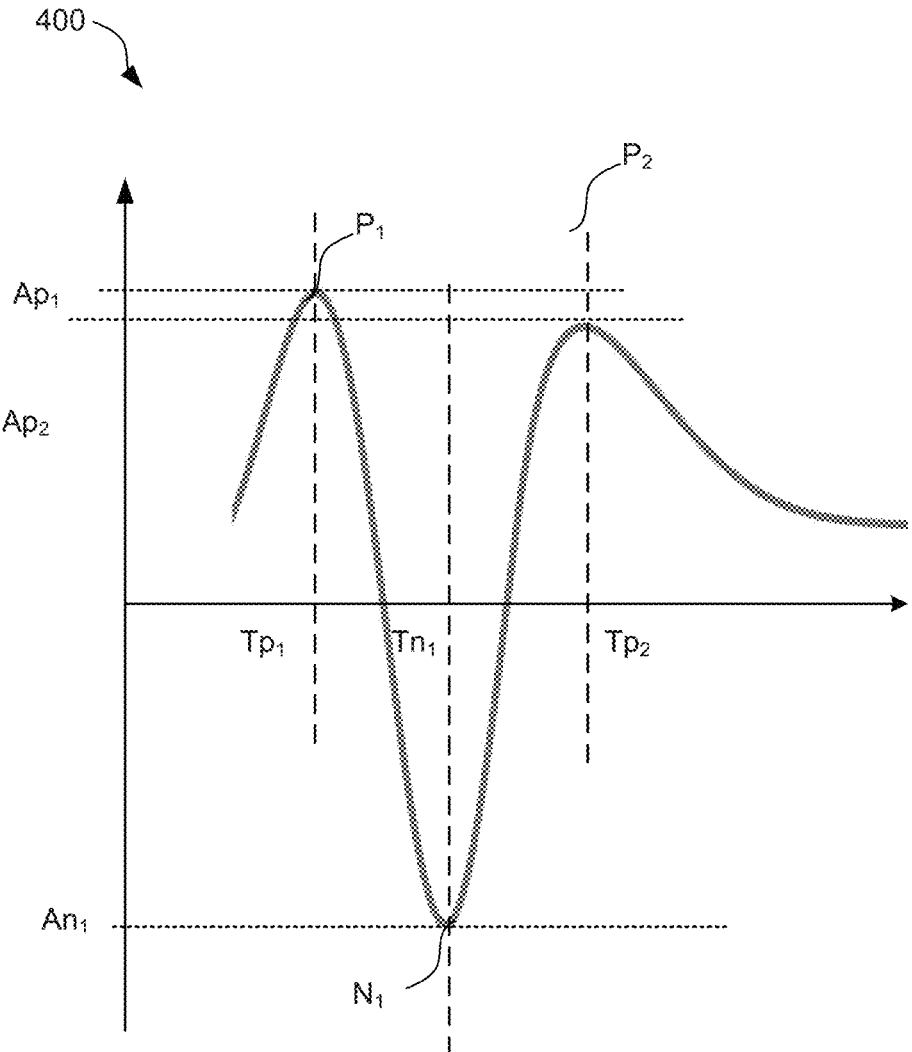
FIG. 4 illustrates the typical form of an ECAP of a healthy subject, in accordance with an embodiment.

FIG. 4 illustrates the typical form of an ECAP 400 of a healthy subject, as recorded at a single measurement electrode referenced to the system ground 130, in accordance with an embodiment. The shape and duration of the singleended ECAP 400 shown in FIG. 4 is predictable because it is a result of the ion currents produced by the ensemble of fibres depolarising and generating action potentials (APs) in response to stimulation. The evoked action potentials (EAPs) generated synchronously among a large number of fibres sum to form the ECAP 400. The ECAP 400 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Depending on the polarity of recording, a differential ECAP may take an inverse form to that shown in FIG. 4, i.e. a form having two negative peaks N1 and N2, and one positive peak P1. Alternatively, depending on the distance between the two measurement electrodes, a differential ECAP may resemble the time derivative of the ECAP 400, or more generally the difference between the ECAP 400 and a time-delayed copy thereof.

The ECAP 400 may be characterised by any suitable characteristic(s) of which some are indicated in FIG. 4. The amplitude of the positive peak P1 is $Ap_1$ and occurs at time $Tp_1$. The amplitude of the positive peak P2 is Ape and occurs at time $Tp_2$. The amplitude of the negative peak P1 is $An_1$ and occurs at time $Tn_1$. The peak-to-peak amplitude is $Ap_1+An_1$. A recorded ECAP will typically have a maximum peak-to-peak amplitude in the range of microvolts and a duration of 2 to 3 ms.

Figure 5:
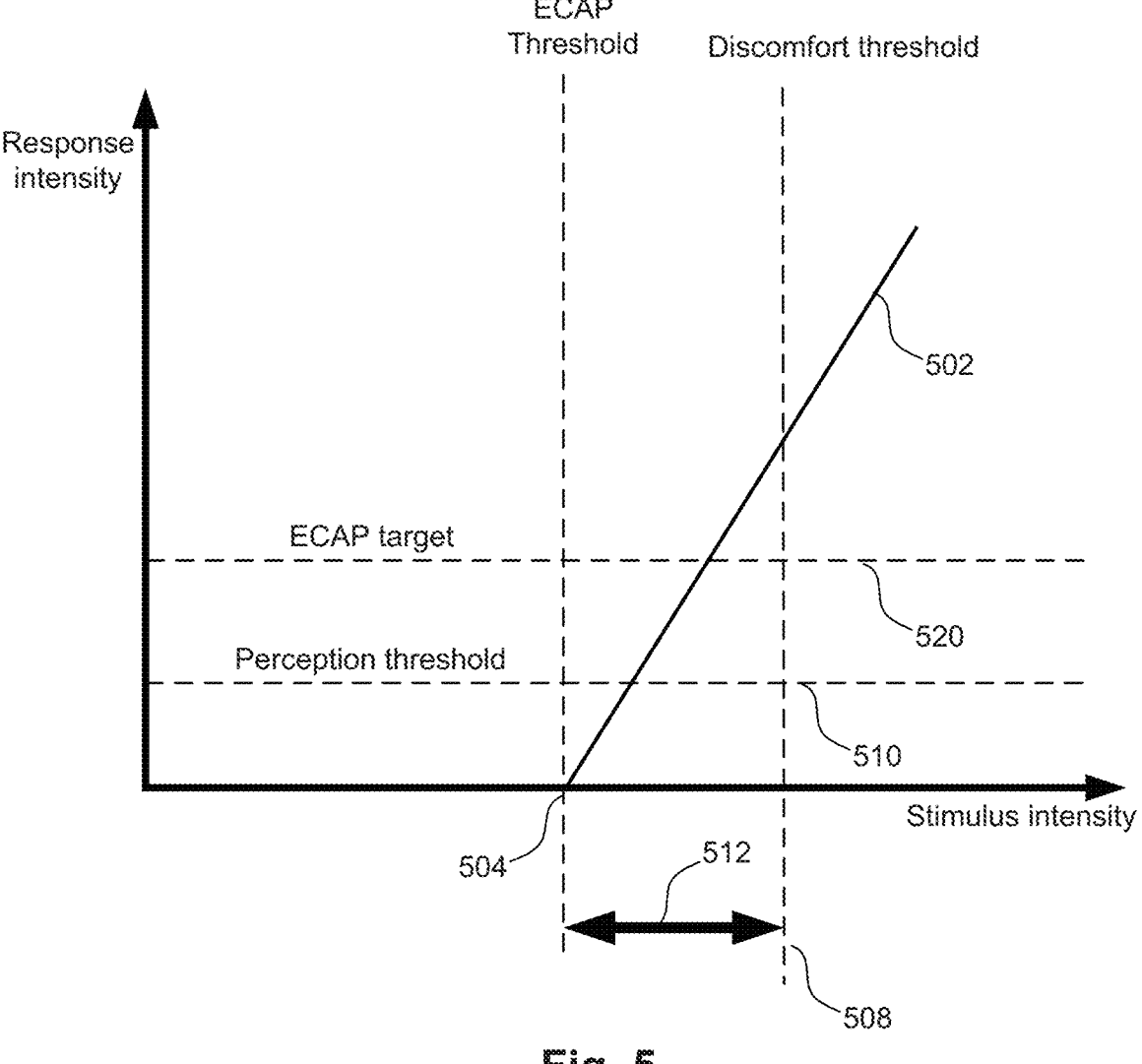
FIG. 5 illustrates an activation plot, in accordance with an embodiment.

FIG. 5—Activation Plots

FIG. 5 illustrates an activation plot 502, in accordance with an embodiment. An activation plot, or growth curve, is an approximation to the relationship between stimulus intensity (e.g. an amplitude of the current pulse 160) and intensity of neural response 170 resulting from the stimulus (e.g. an ECAP amplitude). FIG. 5 illustrates an idealised activation plot 502 for one posture of the patient 108. The activation plot 502 shows a linearly increasing ECAP amplitude for stimulus intensity values above a threshold 504 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 504 therefore reflects the field strength at which significant numbers of fibres begin to be recruited, and the increase in response intensity with stimulus intensity above the ECAP threshold reflects increasing numbers of fibres being recruited. Below the ECAP threshold 504, the ECAP amplitude may be taken to be zero. Above the ECAP threshold 504, the activation plot 502 has a positive, approximately constant slope indicating a linear relationship between stimulus intensity and the ECAP amplitude. Such a relationship may be modelled as:

$$y = \begin{cases} S(s-T), & s \geq T \\ 0, & s < T \end{cases} \tag{1}$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 502.

FIG. 5 also illustrates a discomfort threshold 508, which is a stimulus intensity above which the patient 108 experiences uncomfortable or painful stimulation. FIG. 5 also illustrates a perception threshold 510. The perception threshold 510 corresponds to an ECAP amplitude that is perceivable by the patient. There are a number of factors which can influence the position of the perception threshold 510, including the posture of the patient. Perception threshold 510 may correspond to a stimulus intensity that is greater than the ECAP threshold 504, as illustrated in FIG. 5, if patient 108 does not perceive low levels of neural activation. Conversely, the perception threshold 510 may correspond to a stimulus intensity that is less than the ECAP threshold 504, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it may be desirable to maintain stimulus intensity within a therapeutic range. A stimulus intensity within a therapeutic range 512 is above the ECAP threshold 504 and below the discomfort threshold 508. In principle, it may be straightforward to measure these limits and ensure that stimulus intensity, which may be closely controlled, always falls within the therapeutic range 512. However, the activation plot, and therefore the therapeutic range 512, varies with the posture of the patient 108.

Figure 6:
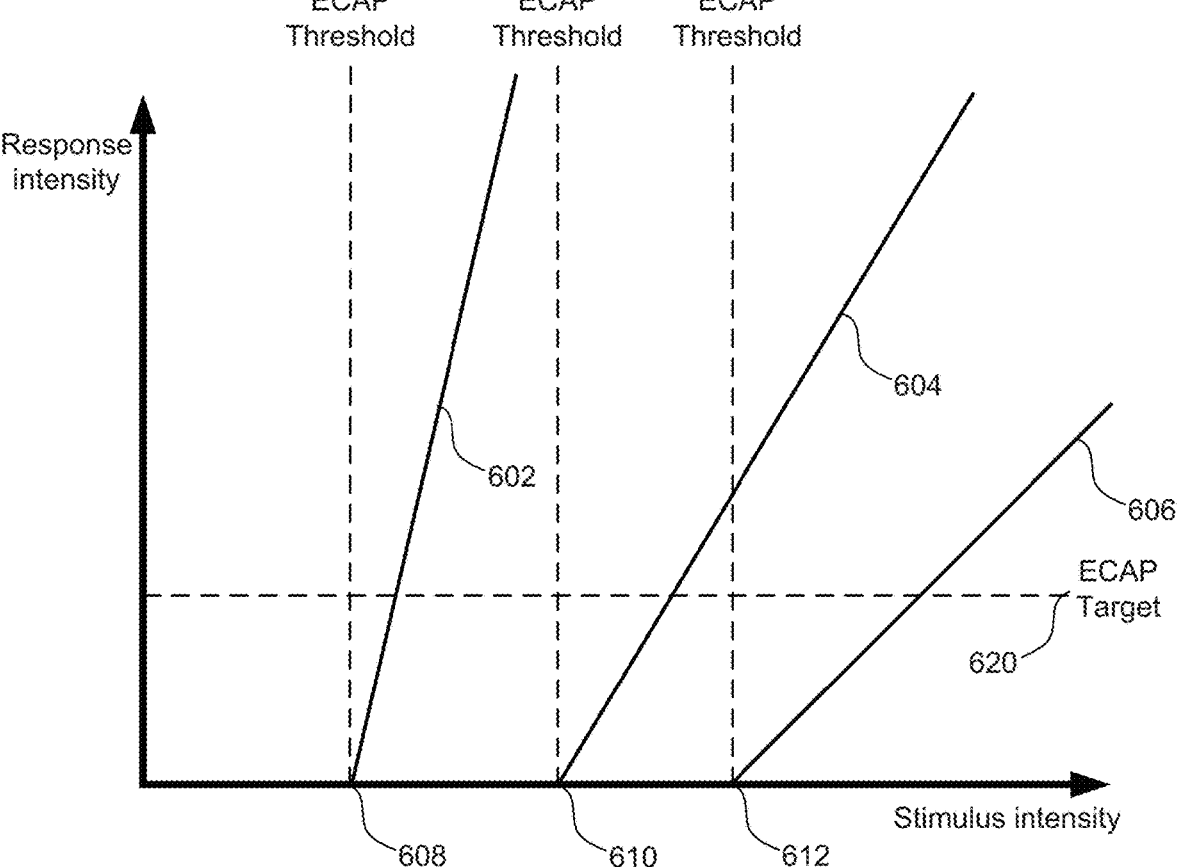
FIG. 6 illustrates the variation in the activation plots with changing posture of the patient, in accordance with an embodiment.

FIG. 6—Changing Posture

FIG. 6 illustrates the variation in the activation plots with changing posture of the patient, in accordance with an embodiment. A change in posture of the patient may cause a change in impedance of the electrode-tissue interface or a change in the distance between electrodes and the neurons. While the activation plots for only three postures, 602, 604 and 606, are shown in FIG. 6, the activation plot for any given posture can lie between or outside the activation plots shown, on a continuously varying basis depending on posture. Consequently, as the patient's posture changes, the ECAP threshold changes, as indicated by the ECAP thresholds 608, 610, and 612 for the respective activation plots 602, 604, and 606. Additionally, as the patient's posture changes, the slope of the activation plot also changes, as indicated by the varying slopes of activation plots 602, 604, and 606. In general, as the distance between the stimulus electrodes and the spinal cord increases, the ECAP threshold increases and the slope of the activation plot decreases. The activation plots 602, 604, and 606 therefore correspond to increasing distance between stimulus electrodes and spinal cord, and decreasing patient sensitivity.

Figure 7:
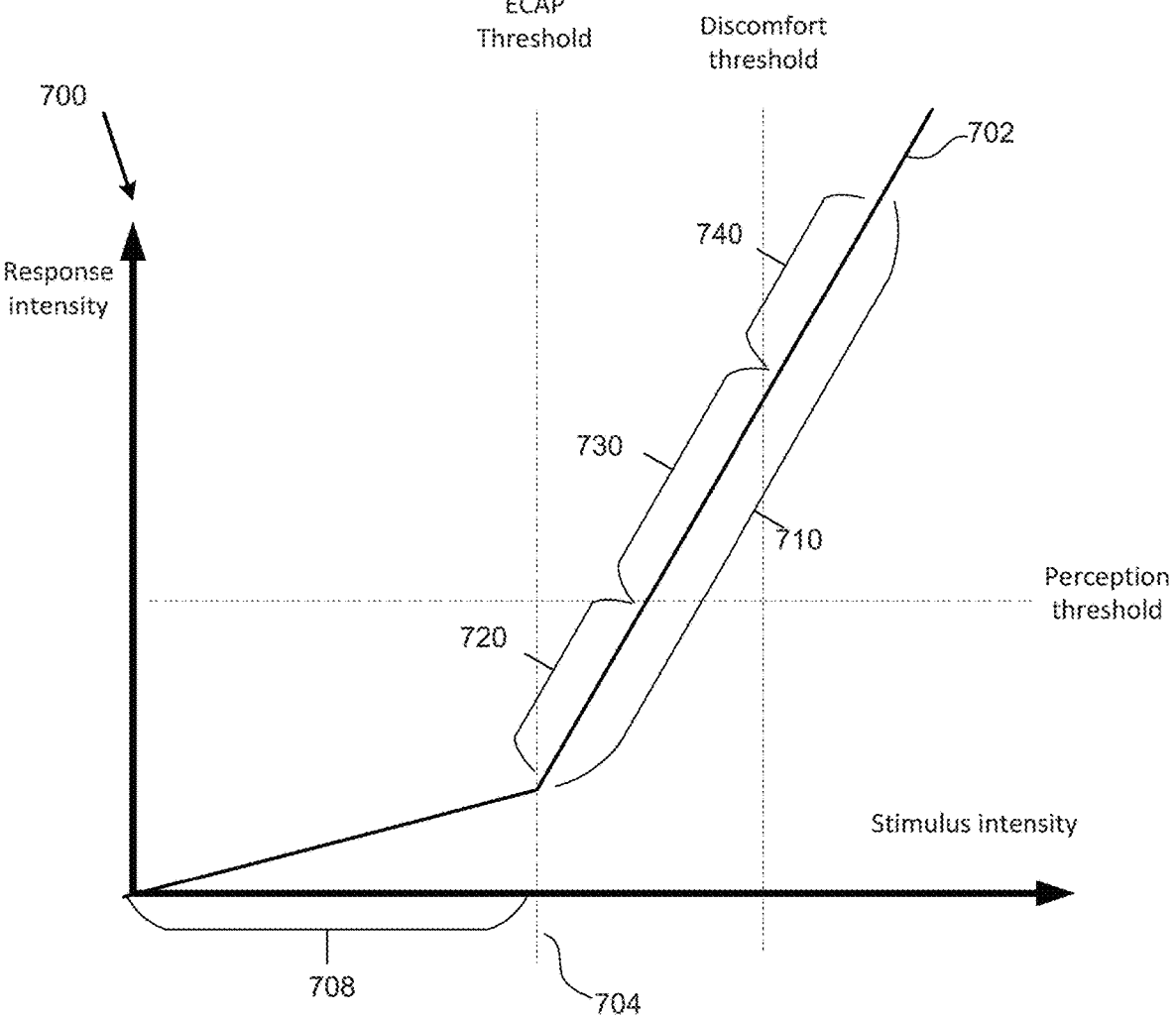
FIG. 7 illustrates a linear approximation of an activation plot, in accordance with an embodiment.

FIG. 7—Regions of Operation

FIG. 7 is a graph illustrating a linear approximation of an activation plot 702, in accordance with an embodiment. The plot 702 has an ECAP threshold at the stimulus current level 704, meaning that for stimulus currents at levels below stimulus current level 704 the resulting intensity of neural response is below the level at which an ECAP amplitude may be measured. This may be because the ECAP component of the sensed signal cannot be differentiated from the artefact and noise at this low level.

The plot 702 comprises at least two regions of operation, namely a sub-ECAP-threshold (sub-threshold) region 708 and a supra-ECAP-threshold (supra-threshold) region 710. For some embodiments, it may be advantageous to consider that the plot 702 comprises more than two regions of operation, namely a sub-ECAP-threshold (sub-threshold) region 708, a supra-ECAP-threshold region 720 and a supra-perception-threshold region 730. The supra-perception-threshold region 730 extends from the perception threshold to the discomfort threshold. A supra-discomfort-threshold region 740 represents the region of plot 702 which extends above the discomfort threshold. Above the discomfort threshold, the patient may experience uncomfortable or painful stimulation. Accordingly, it is not typically desirable for the set point of the system to be within the supra-discomfort-threshold region 740.

Closed-Loop Neural Stimulation Device

To keep the applied stimulus intensity within the therapeutic range as patient posture varies, in some implementations an implantable neuromodulation device such as the stimulator 100 may adjust the applied stimulus intensity based on a feedback variable that is determined from one or more measured ECAP characteristics. In one implementation, the device may adjust the stimulus intensity to maintain the measured ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on a measured ECAP characteristic is said to be operating in closed-loop mode and will also be referred to as a closed-loop neural stimulation (CLNS) device. By adjusting the applied stimulus intensity to maintain the measured ECAP amplitude at an appropriate target response intensity, such as a target ECAP amplitude 520 illustrated in FIG. 5, a CLNS device will generally keep the stimulus intensity within the therapeutic range as patient posture varies.

A CLNS device comprises a stimulator that takes a stimulus intensity value and converts the stimulus intensity value into a neural stimulus comprising a sequence of electrical pulses according to a predefined stimulation pattern. The stimulation pattern is parametrised by multiple parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The intensity of an evoked neural response (e.g. an ECAP) is detected, and its amplitude measured by the CLNS device and compared to the target response intensity.

The measured neural response intensity, and its deviation from the target response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 8:
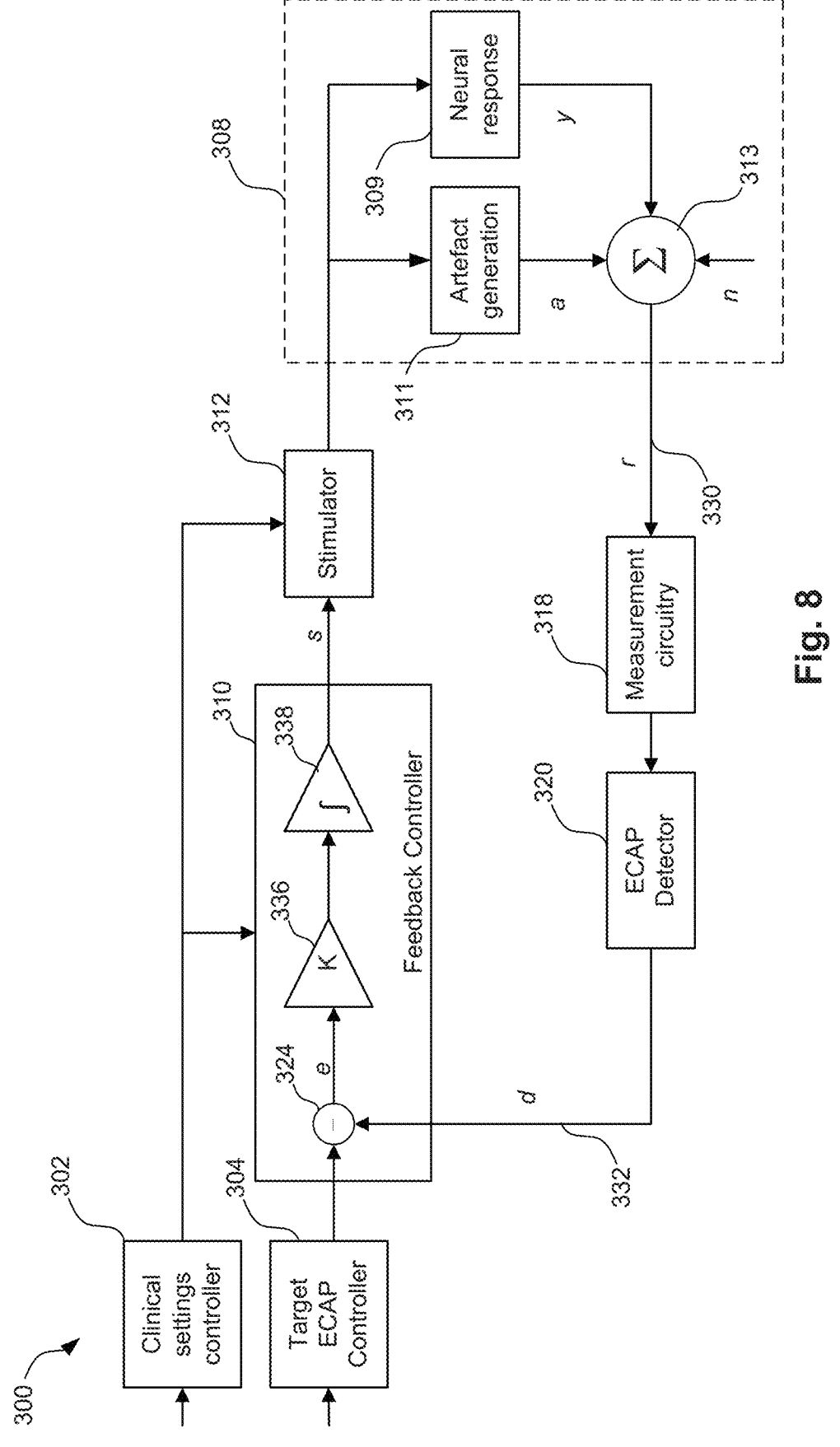
FIG. 8 schematically illustrates elements and inputs of a closed-loop neural stimulation (CLNS) system, in accordance with an embodiment.

FIG. 8—Example CLNS System

FIG. 8 is a schematic illustrating elements and inputs of a closed-loop neural stimulation (CLNS) system 300, in accordance with an embodiment. The CLNS system 300 is implemented as part of the electronics module 110. The CLNS system 300 comprises a stimulator 312 (otherwise called a stimulus source) which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 8). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. The nature and form of artefacts generated in response to stimulus is described in International Patent Publication No. WO2020/082126 by the present applicant, the contents of which are incorporated herein by reference.

Various sources of measurement noise n, as well as artefact a, may add to the evoked response y at the summing element 313 before the evoked response is measured, including electrical noise from external sources such as 50 Hz mains power; electrical disturbances produced by the body such as neural responses evoked not by the device but by other causes such as peripheral sensory input, EEG, EMG, and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

The measurement circuitry 318, which may be identified with measurement circuitry 128, amplifies the sensed signal r and samples the amplified sensed signal r to capture a "signal window" comprising a predetermined number of samples of the amplified sensed signal r 330. In general, the sensed signal r comprises an ECAP component, and an artefact component. The sensed signal r may further comprise a non-artefact noise component. The ECAP detector 320 processes the signal window and outputs a neural response intensity d 332. In one implementation, the neural response intensity d 332 comprises a peak-to-peak ECAP amplitude. The measured response intensity d is input into the feedback controller 310. The feedback controller 310 comprises a comparator 324 that compares the response intensity d to a target ECAP amplitude (set by the target ECAP controller 304) to provide an indication of the difference between the response intensity d and the target ECAP amplitude. This difference is the error value, e.

The feedback controller 310 calculates an adjusted stimulus intensity parameter, s, with the aim of maintaining a processed response d equal to the target ECAP amplitude. Accordingly, the feedback controller 310 adjusts the stimulus intensity parameters to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be computed by the feedback controller 310 as $$s = \int Kedt \qquad (2)$$

where K is the gain of the gain element 336 (the controller gain). This relation may also be represented as $$\delta s = Ke \qquad (3)$$

where δs is an adjustment to the current stimulus intensity parameter s.

A target ECAP amplitude is input to the comparator 324 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the CLNS system 300, via which the patient or clinician can input a target ECAP amplitude, or indication thereof. The target ECAP controller 304 may comprise memory in which the target ECAP amplitude is stored, and from which the target ECAP amplitude is provided to the feedback controller 310.

A clinical settings controller 302 provides clinical settings to the system 300, including the gain K for the gain element 336 and the stimulus parameters for the stimulator 312. The clinical settings controller 302 may be configured to adjust the gain K of the gain element 336 to adapt the feedback loop to patient sensitivity. The clinical settings controller 302 may comprise an input into the CLNS system 300, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Artefacts

In general, artefacts are signals detected by the electrodes that are not generated by the neural tissue and are not part of the evoked neural response. In some situations, artefacts may be measurements of the stimulation pulses themselves after they are applied to the neural tissue. Depending on the implementation of the stimulation device, artefacts can distort the ECAP measurements as it can be difficult to distinguish the artefact from the evoked neural response.

When an artefact is present in the sensed signal r output by the measurement circuitry 318, the sensed signal comprises a combination of an artefact component and the evoked neural response component (otherwise called the ECAP component). The existence of an artefact component in the sensed signal r may comprise a serious impediment to accurate determination of an ECAP amplitude, which is important for closed-loop neural stimulation.

A number of factors contribute to artefact generation at a given measurement electrode configuration, including the build-up of charge in the tissue or accretion of scar tissue on the stimulus or measurement electrodes. As described in International Patent Publication No. WO2020/082126 by the present applicant, the contents of which are incorporated herein by reference, a mismatch between the impedances of the recording and reference electrodes may increase the artefact component of a sensed signal, and electrode geometry and proximity to the stimulus location may also effect artefact generation. Furthermore, as described in International Patent Publication No. WO2015/168735 by the present applicant, the contents of which are incorporated herein by reference, a too-low input impedance of the ECAP amplifier may increase the artefact component of a sensed signal.

The feedback controller 310 of the CLNS system 300 adjusts the stimulus intensity s for the stimulator 312 based on a difference e between the response intensity d 332 and the target ECAP amplitude. The sensed signal r comprises an artefact component and an ECAP component. The presence of an artefact component within the sensed signal r obscures the amplitude of the ECAP component, which can make it difficult for the CLNS system 300 to determine the ECAP amplitude evoked in the tissue in response to the provided stimulation. As a result, the CLNS system 300 may struggle to determine how to adjust the stimulation to evoke the desired response from subsequent stimulation. Accordingly, in many situations the presence of an artefact component in the sensed signal r is undesirable.

In some embodiments, it may be desirable to mitigate the occurrence of an artefact component in a sensed signal, or at least reduce the magnitude of the artefact component. In other situations, it may be desirable to quantitatively determine the artefact component, such that the presence of the artefact component can be taken into account by the CLNS system when determining the neural response evoked by the stimulus.

Artefact Mitigation Measures

Various artefact mitigation measures (AMMs) may be applied by the stimulator 100 to mitigate artefacts that are present in the sensed signal r 330. Artefact mitigation measures may pre-emptively reduce or eliminate the artefact component from the sensed signal r 330. Artefact mitigation measures may retrospectively separate out, or compensate for the presence of, an artefact component in the sensed signal r 330.

An electronics module of an implantable stimulation device may be configured to apply an artefact mitigation measure by controlling an electrical condition of the tissue to reduce the artefact component of the sensed signal, as measured by the electronics module.

In one embodiment of a pre-emptive AMM, the electronics module 110 controls an electrical condition of the tissue by applying a technique referred to as virtual ground AMM. Methods of applying virtual ground AMM are described in International Patent Publication No. WO2014/071445 by the present applicant, the contents of which are incorporated herein by reference.

The electronics module 110 is configured to apply virtual ground AMM to reduce the artefact by reducing the size of the stimulus crosstalk. In particular, the virtual ground AMM strives to hold the stimulated tissue to a fixed voltage throughout the stimulus cycle so that constant-phase elements (CPEs) at the electrode-tissue interface do not accumulate as much charge as would be the case if the tissue voltage were allowed to float.

In one embodiment, the electronics module 110 is configured to apply virtual ground AMM to the tissue. Accordingly, the electronics module 110 is configured to control an electrical condition of the tissue, by providing a plurality of electrodes including at least one nominal feedback sense electrode and at least one nominal compensation electrode. The feedback sense electrode and the compensation electrode are positioned proximate to the tissue and in electrical contact with the tissue. The electronics module 110 connects a feedback signal from the feedback sense electrode to an input of a feedback amplifier. The amplifier is referenced to a desired electrical value. In one embodiment, the desired electrical value is electrical ground referenced to a patient ground electrode distant from the feedback sense electrode.

The electronics module 110 connects an output of the feedback amplifier to the compensation electrode such that the feedback amplifier drives the tissue via the compensation electrode in a feedback arrangement which seeks to drive the feedback signal to the desired electrical value.

Figure 9:
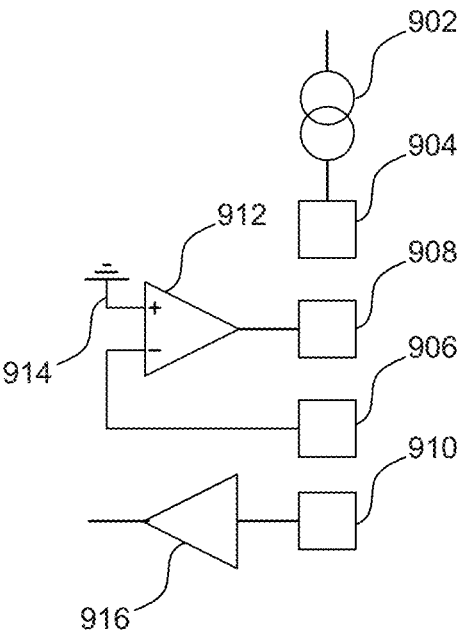
FIG. 9 illustrates a configuration of stimulus and measurement electrodes for controlling electrical conditions of neural tissue, in accordance with an embodiment.

FIG. 9—Virtual Ground Embodiment

FIG. 9 illustrates a configuration of stimulus and measurement electrodes for controlling electrical conditions of neural tissue, in accordance with an embodiment. In the configuration of FIG. 9, the neuromodulation device has a current source 902 which drives current into tissue via stimulus electrode 904 in order to stimulate the neural tissue and evoke a neural response. A feedback sense electrode 906, compensation electrode 908 and measurement electrode 910 are also provided. The electrodes 904-910 are positioned proximate to neural tissue to make electrical contact with the tissue. A feedback amplifier 912 is referenced to ground 914 and takes as an input a feedback signal from the feedback sense electrode 906. An output of the feedback amplifier 912 is connected to the compensation electrode 908 such that the feedback amplifier 912 is configured to drive the tissue via the compensation electrode 908 in a feedback arrangement which seeks to drive the feedback signal to ground. This mechanism will thus operate to quash stimulus artefact at the electrode-tissue interface, improving measurement conditions for neural response measurement circuitry 916.

The adjacent stimulus, compensation, feedback sense and measurement electrodes in contact with resistive tissue can be modelled as respective contacts, each connected to a tissue rail by a respective resistance R1, R2, R3 and R4.

Stimulus and stimulus artefact occurring upon the stimulus electrode 904 creates a current I through R1. Feedback amplifier 912 operates to maintain zero current at each amplifier input, and also operates to maintain the voltage at each input to be identical. Therefore, in the configuration of FIG. 9, the voltage at each amplifier input is zero, because the positive input is referenced to ground. Moreover, current through resistance R3, associated with electrode 906, is forced to zero, being the same as the input current to the amplifier 912. This ensures that there is no voltage differential across R3, and that the tissue node must therefore be forced to ground, in this model. This effect is referred to herein as providing virtual ground.

Artefact Separation

A retrospective method of dealing with undesirable artefacts that distort the ECAP measurement is to apply an artefact mitigation measure that separates artefact present in the sensed signal r from the ECAP component thereof, rather than pre-emptively seeking to eliminate or reduce the artefact at its source.

An electronics module may use an artefact mitigation measure that determines an indication of the artefact component within the sensed signal r, and takes action to separate the artefact component from the ECAP component of the sensed signal r. In one example, the electronics module may use an AMM to computationally extract the ECAP component from a sensed signal that comprises both an ECAP component and an artefact component.

In one embodiment, the ECAP detector 320 of the CLNS system 300 applies a method of separating the ECAP component of the sensed signal 330 from the artefact component of the sensed signal 330 via a basis element signal separation (BESS) approach. A BESS-based detector 320 estimates the underlying component signals of the sensed signal 330 given only the sensed signal 330, and without knowledge of the exact underlying ECAP and artefact component signals or their relative intensities. Various BESS-based detectors are described in International Patent Publication No. WO2020/124135 by the same applicant, the contents of which are incorporated herein by reference.

In one embodiment, the electronics module 110 applies a BESS-based detector by assuming that each underlying signal may be expressed as a linear combination of basis functions. To separate the artefact component within the sensed signal, the CLNS system can comprise a BESS-based detector 320. In some embodiments, BESS-based detector 320 comprises a computational process for separating the ECAP component from the artefact component within the sensed signal 330. In some embodiments, the BESS-based detector may comprise a method for removing the separated artefact from the sensed signal 330. In some embodiments, the BESS-based detector 320 is implemented by the controller 116, configured by control programs 122 of the implanted stimulator 100.

Artefact Compensation

Another artefact mitigation measure (AMM), referred to herein as artefact compensation, compensates for an artefact component in the sensed signal r by adding an artefact compensation parameter to the response intensity d. Artefact compensation is described in International Patent Publication No. WO2022/040754, the contents of which are incorporated herein by reference, and in International Patent Publication No. WO2022/040753, the contents of which are incorporated herein by reference.

The artefact compensation parameter is configured to nullify, or at least partially nullify, the artefact component of the response intensity d. The signal resulting from the addition of the response intensity d and the artefact compensation parameter is a signal that is representative of the ECAP component of the sensed signal r.

In one embodiment, the detector 320 is configured to add an artefact compensation parameter to the response intensity d. In one embodiment, the artefact compensation parameter, is configured to be proportional to the stimulus current, s, and is of opposite sign and equivalent magnitude to the estimated artefact component, a. The artefact compensation parameter can be adjusted by use of a factor $K_a$, which is the negative of the gain rate between the stimulus waveform and the detector output.

The response intensity d is added to the artefact compensation parameter to produce an adjusted response intensity d'. The artefact compensation parameter nullifies, or partially nullifies, the presence of the artefact component, and the adjusted response intensity d' represents the ECAP component of the sensed signal r.

Cost of AMMS

Artefact mitigation measures incur an operational cost, in terms of power consumption and processing complexity. For example, the application of the virtual ground AMM consumes power as the electronics module 110 drives the feedback signal to ground. Furthermore, the artefact separation and artefact compensation AMMs consume power and processor cycles via additional computations.

In some embodiments, the stimulator 100 is powered by a rechargeable battery. Accordingly, the consumption of power by artefact mitigation measures may drain the battery at a faster rate, than would otherwise occur without the application of artefact mitigation measures. Draining the battery at a fast rate may shorten the charge interval of the stimulation device. Additionally, in some embodiments, the activation of an AMM can increase non-artefact noise and thereby worsen the signal-to-noise ratio of the sensed signal r. Accordingly, for some embodiments, it may be desirable to only apply AMMs selectively, rather than applying AMMs constantly.

AMM Activation Status

In some embodiments, it may be desirable to determine situations in which the application of AMMs will, or is likely to, provide a sufficiently advantageous mitigation of an artefact component. In such situations, the application of AMMs may still be considered advantageous even though the application of AMMs consumes additional power.

In one embodiment, the electronics module 110 is configured with a setting that indicates whether to apply AMMs. This setting is referred to as the AMM activation status (or 'activation status' or 'artefact mitigation status'). In response to the activation status indicating active, the electronics module 110 is configured to apply an artefact mitigation measure. In response to the activation status indicating inactive, the electronics module 110 is configured to not apply an artefact mitigation measure.

The electronics module 110 may further be configured to retain an indication of the type of AMM to apply, in response to the activation status indicating active. This setting is referred to as the AMM type. The AMM type may be set to, for example: virtual ground, BESS artefact separation, artefact compensation, or another artefact mitigation measure. The electronics module 110 may be configured to determine the activation status and AMM type settings, for example, during stimulation. Alternatively, electronics module 110 may be configured with the activation status and AMM type settings via the clinical settings 302.

In one embodiment, the activation status is defined by the clinical settings 302, and the electronic module 110 is configured retain the activation status in accordance with the clinical settings 302. Configuration of the electronics module 110 in accordance with the clinical settings 302 is described further in relation to FIG. 14.

Determining the Activation Status

In some embodiments, the electronics module 110 is configured to determine the AMM activation status. In some embodiments, the activation status is determined by a software application which configures the clinical settings 302. The software application may comprise a Clinical Programming Application (CPA), executing on external computing device 192 of FIG. 1.

The electronics module 110 is configured to be programmed in accordance with the clinical settings 302, including the AMM activation status, and to apply artefact mitigation measures in accordance with the AMM activation status.

In one embodiment, the activation status is determined based on a consideration of whether the activation of AMM results in sufficiently advantageous mitigation of the artefact. For example, the artefact-to-ECAP ratio of the sensed signal with AMM activated may be compared with the artefact-to-ECAP ratio of the sensed signal with AMM inactive to determine whether a sufficiently advantageous mitigation of the artefact results from the activation of AMM. In circumstances in which AMM fails to sufficiently mitigate the artefact, the activation status may be set to 'inactive' to conserve power and computation cycles. Similarly, in circumstances in which the artefact component without AMM activated is sufficiently negligible with respect to the ECAP component, the activation status may be set to 'inactive' to conserve power and computation cycles.

In another embodiment, the activation status is determined based on an estimated level of artefact that will be produced as a result of performing stimulation. If the estimated level of artefact is sufficiently high, the activation status may be set to 'active' to mitigate the artefact.

A determination of whether an artefact is sufficiently high, or is sufficiently mitigated, or is sufficiently negligible with respect to the ECAP component may be influenced by a number of factors, which may include the clinical settings for the particular patient, the power usage settings for the implantable device, the remaining battery power, the posture of the patient, or the posture variation behaviour of the patient. In one embodiment, the electronics module 110 is configured with threshold values which define values at which the artefact is sufficiently high, or is sufficiently mitigated, or is sufficient negligible with respect to the ECAP component.

Figure 10:
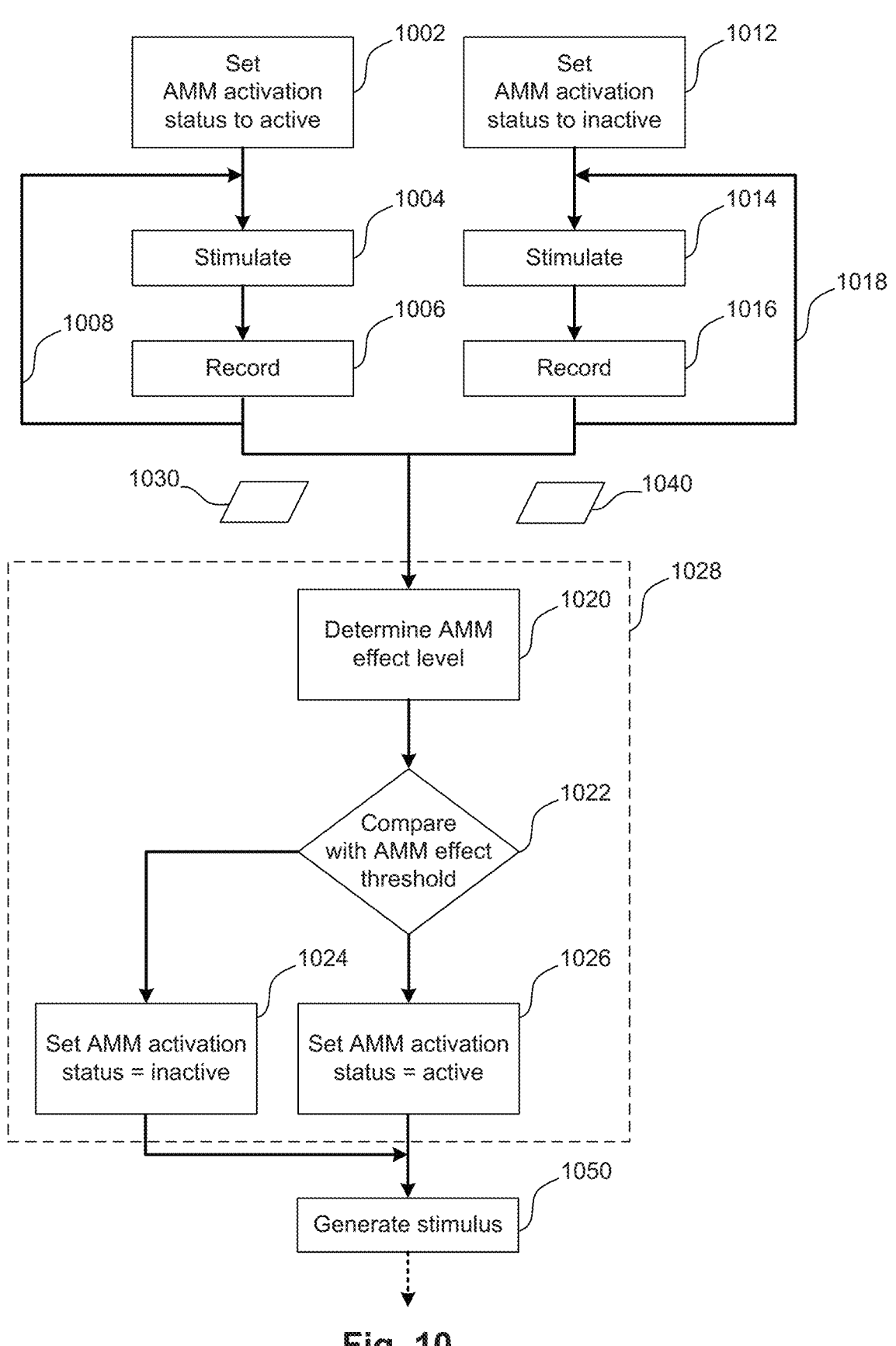
FIG. 10 illustrates a method for determining an artefact mitigation status, in accordance with an embodiment.

FIG. 10—Comparative Determination of Activation Status

FIG. 10 illustrates a method 1000, as performed by the electronics module 110, for determining an artefact mitigation status, in accordance with an embodiment. Method 1000 compares the sensed signal r when an artefact mitigation measure is activated, with the sensed signal r when the artefact mitigation measure is not activated to determine whether it is beneficial to activate the artefact mitigation measure. The method 1000 is particularly suitable for pre-emptive AMMs such as virtual ground.

In step 1002, the electronics module 110 configures the AMM activation status to be active, meaning that the electronics module 110 is configured to apply one or more artefact mitigation measures. In step 1004, the electronics module 110 applies a stimulus to the neural tissue with the AMM activated. In one example, the AMM comprises virtual ground artefact mitigation measure, and the electronics module 110 applies the stimulus to the tissue while controlling an electrical condition of the neural tissue. In step 1006, the electronics module 110 records a sensed signal r 330 of the neural tissue, subsequent to the stimulus applied in step 1004.

The electronics module 110 may perform steps 1004 and 1006 iteratively, as indicated by path 1008, to obtain a plurality of stimulation data points with AMM activated. The plurality of stimulation data points make up stimulation data set 1030. Each stimulation data point of data set 1030 comprises a data couple comprising stimulus parameters, including stimulus intensity s, and the corresponding sensed signal r of the neural tissue evoked by the stimulus.

In step 1012, the electronics module 110 configures the AMM activation status to be inactive, meaning that the electronics module 110 is configured to not apply artefact mitigation measures. In step 1014, the electronics module 110 applies a stimulus to the neural tissue. The stimulus applied in step 1014 may be the same as the stimulus applied in step 1004. In step 1016, the electronics module 110 records a sensed signal r 330 of the neural tissue, subsequent to the stimulus applied in step 1014.

The electronics module 110 may perform steps 1014 and 1016 iteratively, as indicated by path 1018, to obtain a plurality of stimulation data points, comprising stimulation data set 1040, with AMM inactive.

Steps 1020, 1022, 1024 and 1026 (collectively referred to as steps 1028) consider the stimulation data sets 1030 and 1040 to determine a measure of the effect that the activation of AMM has on the artefact component of the sensed signal r 330. The measure of the effect that the activation of AMM has on the artefact component of the sensed signal is compared with an AMM effect threshold to determine whether it is desirable to proceed with stimulation with AMM active or inactive.

Steps 1028 are described herein as being performed by the electronics module 110; however, in an alternative example, steps 1028 may be performed by an external entity, such as the Clinical Programming Application software executing on external computing device 192 of FIG. 1. In the alternative example, the electronics module 110 transmits stimulation data sets 1030 and 1040 to the external computing device 192, so that the Clinical Programming Application software may perform steps 1028. After reaching step 1024 or 1026, the Clinical Programming Application software adjusts the clinical settings 302 to configure the electronics module 110 to activate AMM (in the case of method 1000 reaching step 1026) or not activate AMM (in the case of method 1000 reaching step 1024).

Determining an AMM Effect Level

In step 1020, the electronics module 110 processes stimulation data sets 1030 and 1040 to determine an AMM effect level. An AMM effect level may comprise a comparison measure of the quantity of artefact present in sensed signals generated with AMM activated (represented by data set 1030) compared to the quantity of artefact present in sensed signals generated with AMM inactive (represented by data set 1040).

In one embodiment, the electronics module 110 determines an AMM effect level as a ratio of an aggregate artefact measure of the data points of stimulation data set 1030 to an aggregate artefact measure of the data points of stimulation data 1040.

In one embodiment, the electronics module 110 determines an AMM effect level as a ratio of an aggregate artefact-to-ECAP ratio of the data points of stimulation data set 1030 to an aggregate artefact-to-ECAP ratio of the data points of stimulation data 1040.

Determining Artefact-to-ECAP Ratio

In one embodiment, the electronics module 110 determines the artefact-to-ECAP ratio of each stimulation data point in stimulation data sets 1030 or 1040 by separating the ECAP component of the sensed signal 330 from the artefact component of the sensed signal 330 via a basis element signal separation (BESS)-based detector as described above. The BESS-based detector estimates the underlying component signals of the sensed signal 330 given only the sensed signal 330, and without knowledge of the exact underlying ECAP and artefact component signals. Various BESS-based detectors are described in the above-mentioned International Patent Publication No. WO2020/124135.

The artefact-to-ECAP ratio of each stimulation data point in a stimulation data set, 1030 or 1040, may be aggregated, or averaged, to determine an artefact-to-ECAP ratio that is indicative of the artefact-to-ECAP ratio of the entire data set.

In one embodiment, the electronics module 110 determines the artefact-to-ECAP ratio of stimulation data points in a stimulation data set by applying the ECAP detector 320 to the sensed signal r in each data point to measure a response intensity d corresponding to each stimulus intensity s. In this embodiment, the ECAP detector 320 may include a certain amount of artefact while measuring the response intensity d. The electronics module 110 then fits a growth curve model that takes artefact into account to the set of (s, d) pairs. A growth curve model that takes artefact into account (an artefact-aware growth curve model) is described in the above-mentioned International Patent Publication No. WO2022/040754 by the same applicant, the contents of which are incorporated herein by reference.

In one example, the artefact-aware growth curve model comprises a piecewise linear model with at least a sub-threshold region and a supra-threshold region as illustrated in FIG. 7. In one embodiment, the artefact-aware growth curve model separates the artefact component of each sensed signal from the ECAP component using the two regions of the artefact-aware growth curve. The electronics module 110 computes a ratio of the artefact components obtained from the artefact-aware growth curve model to the ECAP components obtained from the artefact-aware growth curve model over the stimulation data set.

In one embodiment, the electronics module 110 determines the artefact-to-ECAP ratio of stimulation data points in a stimulation data set by applying the ECAP detector 320 to the sensed signal in each data point to obtain a response intensity d corresponding to each stimulus intensity s. In this embodiment, the ECAP detector 320 is configured to reject artefact while measuring the response intensity d. One such ECAP detector 320 is the BESS-based detector 320 mentioned above. The electronics module 110 then fits a no-artefact growth curve model (e.g. a growth curve model as illustrated in FIG. 5 that is zero below the ECAP threshold and rises linearly above the ECAP threshold) to the set of (s, d) pairs. The no-artefact growth curve model produces a set of residuals. The residuals may follow a distribution that indicates the presence of an artefact component in the sensed signals. The electronics module 110 computes a ratio of residuals to the fitted response intensities over the stimulation data set.

AMM Effect Threshold

In step 1022, the electronics module 110 compares the AMM effect level, determined in step 1020, to an AMM effect threshold, to determine whether it would be advantageous to activate an AMM. In one embodiment, the clinical settings 302 define the AMM effect threshold. In one embodiment the electronics module 110 is configured to retain an indication of the AMM effect threshold. The AMM effect threshold may be calculated from ECAP component, artefact component, and/or residual noise levels obtained from prior patient data without any AMM in use.

In one embodiment, in response to the AMM effect level exceeding the AMM effect threshold, the electronics module 110 proceeds to step 1026 and sets the AMM activation status to active. In response to the AMM effect level not exceeding the AMM effect threshold, the electronics module 110 proceeds to step 1024 and sets the AMM activation status to inactive.

In Step 1050, the electronics module 110 generates a stimulus. In response to the AMM activation status being active, the electronics module 110 applies one or more artefact mitigation measures in step 1050. In response to the AMM activation status being inactive, the electronics module 110 does not apply an artefact mitigation measure in step 1050.

Sub-Threshold Stimulation

The AMM effect level may be determined by comparing stimulation data sets 1030 and 1040 that have been generated by stimulation at a sub-threshold level. As described in relation to FIG. 7, stimulation in the sub-threshold region of an activation plot results in a measured ECAP component of the sensed signal 330 being below a signal-to-noise threshold. Accordingly, the true ECAP component may be zero for a sensed signal generated in response to stimulation generated in the sub-threshold region of an activation plot.

In one embodiment, the electronics module 110 is configured to generate stimulus in steps 1004 and 1014 in the sub-threshold region of an activation plot associated with the tissue. Accordingly, the sensed sub-threshold signal 330 recorded by the electronics module 110 in steps 1006 and 1016, comprises an artefact component and non-artefact, or residual, noise, but no ECAP component. The artefact component in a sensed sub-threshold signal 330 may be separated from residual noise by a basis element signal separation (BESS)-based detector as described above. Alternatively, the residual noise in a sensed sub-threshold signal may be obtained by taking an average of the ensemble of sensed sub-threshold signals and subtracting the average from the sensed sub-threshold signal. Based on the stimulation data set 1030, the electronics module 110 determines an indication of the amount of artefact and the amount of residual noise present in each sensed sub-threshold signal with an AMM activated. Similarly, based on the stimulation data set 1040, the electronics module 110 determines an indication of the residual noise present in each sensed sub-threshold signal with AMM inactivated. The artefact-to-noise ratio of each sensed sub-threshold signal in a stimulation data set, 1030 or 1040, may be aggregated, or averaged, to determine an artefact-to-noise ratio that is indicative of the artefact-to-noise ratio of the entire data set. The AMM effect level, determined in step 1020, comprises a ratio of the artefact-to-residual-noise ratio present in the sensed sub-threshold signals with AMM activated, and the artefact-to-residual-noise ratio present in the sensed sub-threshold signals with AMM inactivated. Alternatively, the AMM effect level, determined in step 1020, comprises a ratio of the aggregate artefact amount present in the sensed sub-threshold signals with AMM activated, and the aggregate artefact amount present in the sensed sub-threshold signals with AMM inactivated.

Posture Dependence

The activation of artefact mitigation measures may be advantageous in scenarios in which the magnitude of the artefact component is quite sensitive to the posture of the patient during stimulation. A patient may receive stimulation when in a variety of postures, including prone, standing, supine and sitting. A change in posture of the patient may cause a change in impedance of the electrode-tissue interface or a change in the distance between electrodes and the neurons. This change in impedance or distance may result in a change in the magnitude of the artefact component of the sensed signal. Accordingly, it may be advantageous to determine the susceptibility of the CLNS loop to posture-induced artefact variation and to activate AMMs when the patient is in (or is anticipated to be in) a posture which results in an increased artefact component.

The relationship between artefact generation and the patient's posture may be unique to each particular patient, and may vary over time with electrode movement, or the accretion of scar tissue on the electrode. To determine the relationship between artefact generation and the patient's posture, the electronics module 110 may be configured to perform a plurality of iterations of steps 1004, 1006, 1014, and 1016, while the patient assumes one of a plurality of different postures per iteration. Such a process may be performed during a configuration, or programming, process for the implanted stimulation device. The electronics module 110 may be configured by the Clinical Programming Application software operating on the external computing device 192 of FIG. 1.

In step 1020, the electronics module 110 (or Clinical Programming Application software) processes the stimulation data in the resulting stimulation data sets 1030 and 1040 to determine an indication of the artefact component of the sensed signals. In one embodiment, the artefact component is determined via a basis element signal separation (BESS)-based detector. The electronics module 110 compares the indication of the artefact component for stimulation data sets 1030 and 1040 to determine the effect of posture on the artefact component of the sensed signal, and the effect of the activation of AMMs on the mitigation of the artefact component for each posture tested. In light of this comparison, the electronics module 110, determines an AMM effect level for each posture tested.

In step 1022, for each posture tested, the electronics module 110 compares the AMM effect level to the artefact threshold, to determine, for each posture tested, whether it would be advantageous to activate AMM. Accordingly, the electronics module 110 determines an AMM activation status for each posture tested at step 1024 or step 1026. During stimulation, the electronics module 110 activates or inactivates AMM based on the current (or anticipated) posture of the patient, and based on the AMM activation status for that posture.

The change in posture of a patient may be mimicked by a change in the stimulus parameters. Advantageously, this means that the patient may not actually need to change posture. Accordingly, in one embodiment, the electronics module 110 mimics a change in patient posture by changing the selection of the stimulus electrodes, or the selection of the measurement electrodes, from the plurality of electrodes present on the electrode array 150. For example, the electronics module 110 shifts the selection of the stimulus electrodes to electrodes that are above or below the currently selected electrodes in the rostro-caudal direction to mimic the longitudinal migration along the spinal cord that may occur when a patient changes posture.

The change in posture of a patient may also be mimicked by a change in the number or location of stimulus return electrodes to change the shape of the stimulus field. This may also change the tissue impedance seen by the return electrodes and change the circuit impedance seen by the stimulating electrodes. A change in impedance may be analogous to electrode impedance changes caused by postural variation.

Figure 11:
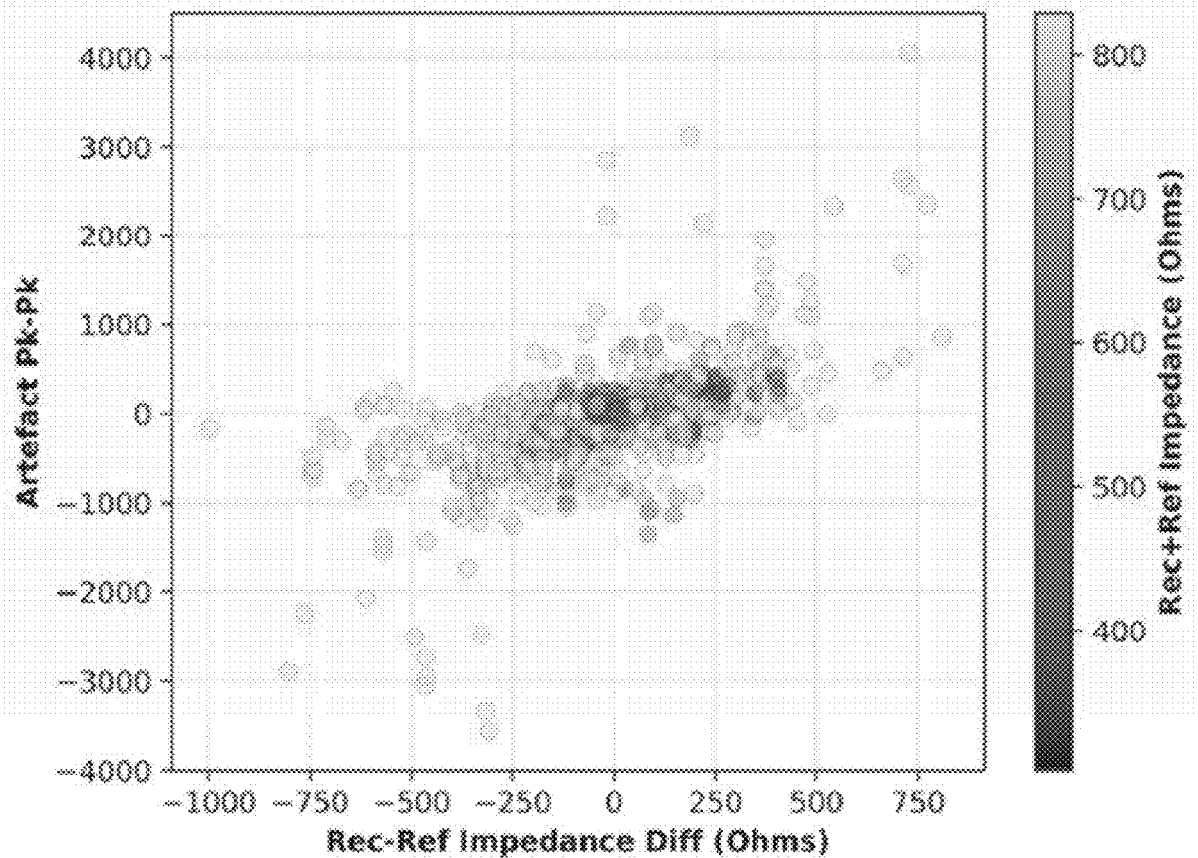
FIG. 11 illustrates a plot of artefact observed in human patients, relative to absolute electrode impedance and relative to an electrode impedance difference, in accordance with an embodiment.

FIG. 11—Artefact Relative to Impedance

The electrode-tissue interface, which is a metal-electrolyte interface, is modelled by a set of constant-phase elements (CPEs). The presence and magnitude of an artefact component in a sensed signal r can be influenced by the CPE impedances of the recording and reference electrodes, as described in International Patent Application No. PCT/AU2022/050347, by the present applicant, the contents of which are incorporated herein by reference.

A difference in the CPE impedance of the recording and reference electrodes may occur due to uneven tissue around the electrodes. The uneven tissue around the electrodes has been observed to increase over time as scar tissue forms around implanted electrodes, but can also be present at the time of implant. Indeed, the present inventors have observed artefact at zero current in human patients, and have also observed that artefact is worse when there is impedance mismatch between the recording electrodes.

FIG. 11 is a plot of artefact observed in human patients, relative to total absolute measurement electrode impedance and relative to a measurement electrode impedance difference $(Zc_1–Zc_2)$, in accordance with an embodiment. The inventors have observed that electrode impedances vary, and that high and mismatched impedances may be associated with high artefact in some embodiments. Patients exhibiting a low impedance on the recording electrodes (dark points) tend not to exhibit high artefact. Patients exhibiting a high total impedance on the recording electrodes (light points) may or may not suffer from high artefact. However, it can be observed that a larger magnitude difference between recording electrode impedances (points at far left or far right of FIG. 11) tend to exhibit a larger magnitude of artefact. Accordingly, if the CPE impedances of the recording and reference electrodes differ, this may be indicative of the anticipated presence of an artefact component in the sensed signal.

Figure 12:
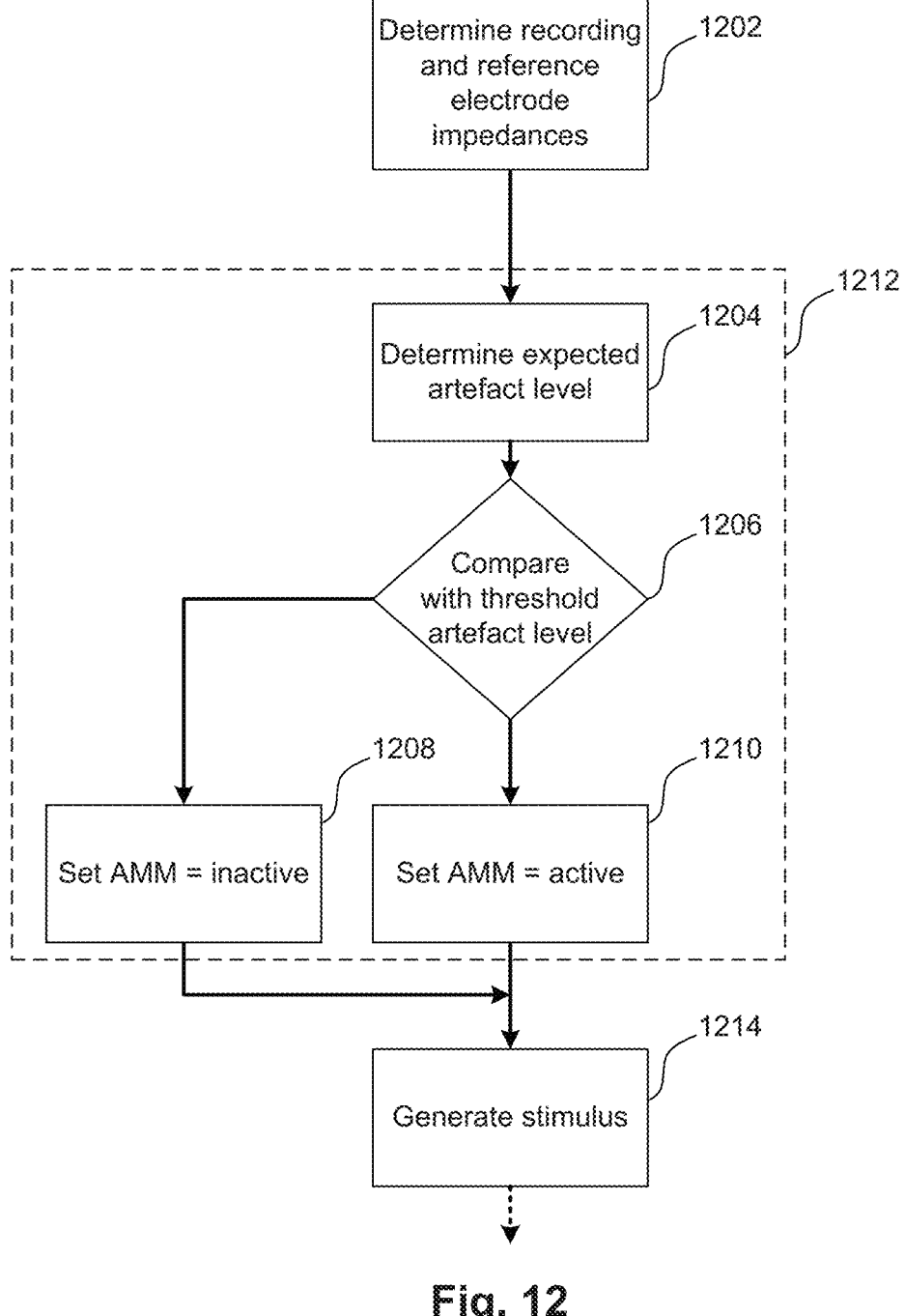
FIG. 12 illustrates a method to set the AMM activation status based on a measured impedance difference, in accordance with an embodiment.

FIG. 12—Determine AMM Activation Status Based on Impedance

The activation status of AMMs may be set based on the impedances of the recording and reference electrodes. For example, the activation status of AMMs may be set based on the impedance difference between the recording and reference electrodes, such that when the impedance difference is greater than an impedance difference threshold, artefact mitigation measures are activated to mitigate the effect of increased artefacts resulting from the impedance difference.

FIG. 12 illustrates a method 1200, as performed by the electronics module 110, to set the AMM activation status based on a measured impedance difference, in accordance with an embodiment. In step 1202, the electronics module 110 determines the impedance $Zc_1$ of the recording electrode, in accordance with a measurement electrode configuration (MEC). In step 1202, the electronics module 110 also determines the impedance $Zc_2$ of the reference electrode, in accordance with the measurement electrode configuration. The impedances of each electrode may be measured using test stimuli and subsequent electrode voltage measurements as described in the above-mentioned International Patent Application No. PCT/AU2022/050347.

In step 1204, the electronics module 110 determines an expected artefact level based on the impedance $Zc_1$ of the recording electrode and the impedance $Zc_2$ of the reference electrode. The expected artefact level may comprise an expected artefact magnitude. In one embodiment, the electronics module 110 determines the expected artefact level as an impedance difference by determining and subtracting the impedance of the reference electrode from the impedance of the recording electrode. In one embodiment, the electronics module 110 determines an expected artefact level as an expected magnitude of artefact based on an input capacitance of the amplifier at the front end of the measurement circuitry 318. The above-mentioned International Patent Application No. PCT/AU2022/050347 describes how to determine an expected magnitude of artefact from the impedance $Zc_1$ of the recording electrode and the impedance $Zc_2$ of the reference electrode and the input capacitance of the amplifier at the front end of the measurement circuitry 318.

In step 1206, the electronics module 110 compares the expected artefact level determined in step 1204 with a threshold artefact level. In one embodiment, in step 1206, the electronics module compares the impedance difference determined in step 1204 with a threshold impedance difference. In one embodiment, the threshold impedance difference is defined by the clinical settings 302, and the electronics module 110 is configured to retain an indication of the threshold impedance difference. In one embodiment, the threshold impedance difference may be computed from a threshold artefact magnitude (otherwise referred to as a threshold magnitude of artefact), as described in the above-mentioned International Patent Application No. PCT/AU2022/050347. In one embodiment, the threshold artefact magnitude is defined by the clinical settings 302, and the electronics module 110 is configured to retain an indication of the threshold artefact magnitude.

If the impedance difference exceeds the threshold impedance difference, the electronics module 110 sets the AMM activation status to active, in step 1210. If the impedance difference does not exceed the threshold impedance difference, the electronics module 110 sets the AMM activation status to inactive, in step 1208.

In one embodiment, step 1204 may compute an expected magnitude of artefact at the maximum expected stimulus intensity using the impedance $Zc_1$ of the reference electrode and the impedance $Zc_2$ of the recording electrode, as described in International Patent Application No. PCT/AU2022/050347. In step 1206, the electronics module 110 compares the expected magnitude of artefact determined in step 1204 with the threshold magnitude of artefact. If the expected magnitude of artefact exceeds the threshold magnitude of artefact, the electronics module 110 sets the AMM activation status to active, in step 1210. If the expected magnitude of artefact does not exceed the threshold magnitude of artefact, the electronics module 110 sets the AMM activation status to inactive, in step 1208.

In one embodiment, steps 1204 to 1210, collectively referred to as steps 1212, are performed by the Clinical Programming Application software rather than by the electronics module 110. In such an embodiment, the electronics module 110 transmits impedance measurements determined in step 1202 to the external computing device 192, so that the Clinical Programming Application software may perform steps 1212. After reaching step 1208 or 1210, the Clinical Programming Application software adjusts the clinical settings 302 to configure the electronics module 110 to activate AMM (in the case of method 1200 reaching step 1210) or inactivate AMM (in the case of method 1200 reaching step 1208).

In step 1214, the electronics module 110 generates a stimulus. In response to the AMM activation status being active, the electronics module 110 applies one or more artefact mitigation measures in step 1214. In response to the AMM activation status being inactive, the electronics module 110 does not apply an artefact mitigation measure in step 1214.

Figure 13:
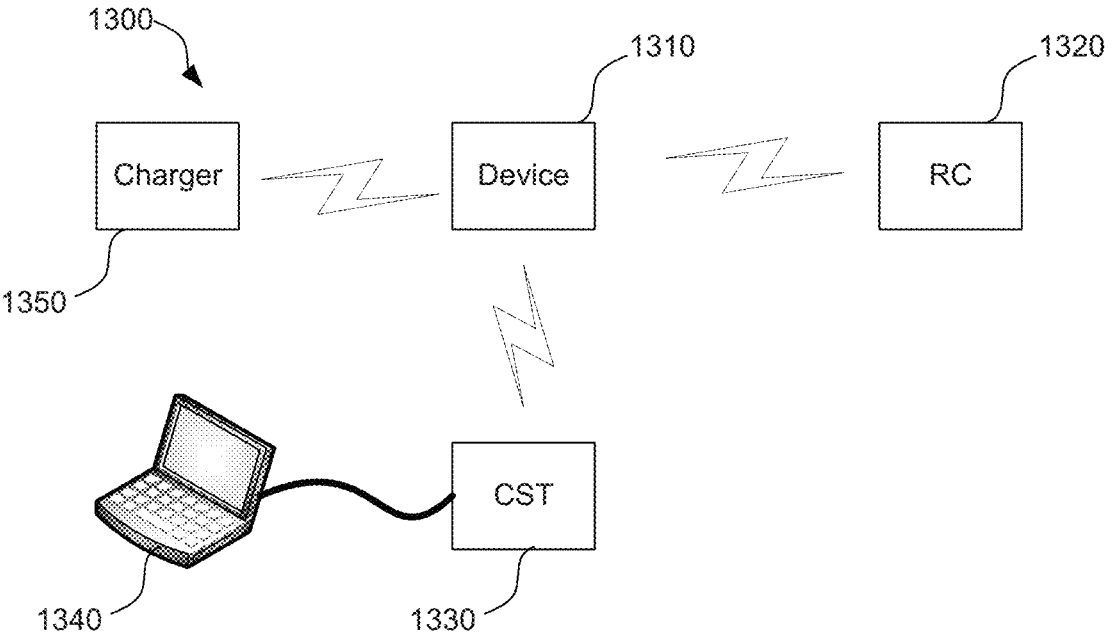
FIG. 13 is a block diagram of a neuromodulation therapy system, in accordance with an embodiment.

FIG. 13—Neuromodulation System

FIG. 13 is a block diagram of a neuromodulation system 1300, in accordance with an embodiment. The neuromodulation system 1300 is centred on a neuromodulation device 1310. In one example, the neuromodulation device 1310 may be implemented as the stimulator 100 of FIG. 1. The neuromodulation device 1310 may be implanted within a patient (not shown).

The neuromodulation device 1310 is connected wirelessly to a remote controller (RC) 1320. If the neuromodulation device 1310 is implanted in a patient, the wireless connection to the RC is transcutaneous. The remote controller 1320 is a portable computing device that provides the patient with control of their stimulation (for example, in the home environment) by allowing control of the functionality of the neuromodulation device 1310, including one or more of the following functions: enabling or disabling stimulation;

adjustment of stimulation intensity; and selection of a stimulation control program from the control programs stored on the neuromodulation device 1310.

The charger 1350 is configured to recharge a rechargeable power source of the neuromodulation device 1310. The recharging is illustrated as wireless in FIG. 13 but may be wired in alternative implementations.

The neuromodulation device 1310 is wirelessly connected to a Clinical System Transceiver (CST) 1330. The wireless connection may be implemented as the transcutaneous communications channel 190 of FIG. 1. The CST 1330 acts as an intermediary between the neuromodulation device 1310 and the Clinical Interface (CI) 1340, to which the CST 1330 is connected. A wired connection is shown in FIG. 13, but in other implementations, the connection between the CST 1330 and the CI 1340 is wireless.

The CI 1340 may be implemented as the external computing device 192 of FIG. 1. The CI 1340 is configured to program the neuromodulation device 1310 and obtain data from the neuromodulation device 1310. This configuration is achieved by program instructions collectively referred to as the Clinical Programming Application (CPA) and stored in an instruction memory of the CI 1340.

FIG. 14—Data Flow

Figure 14:
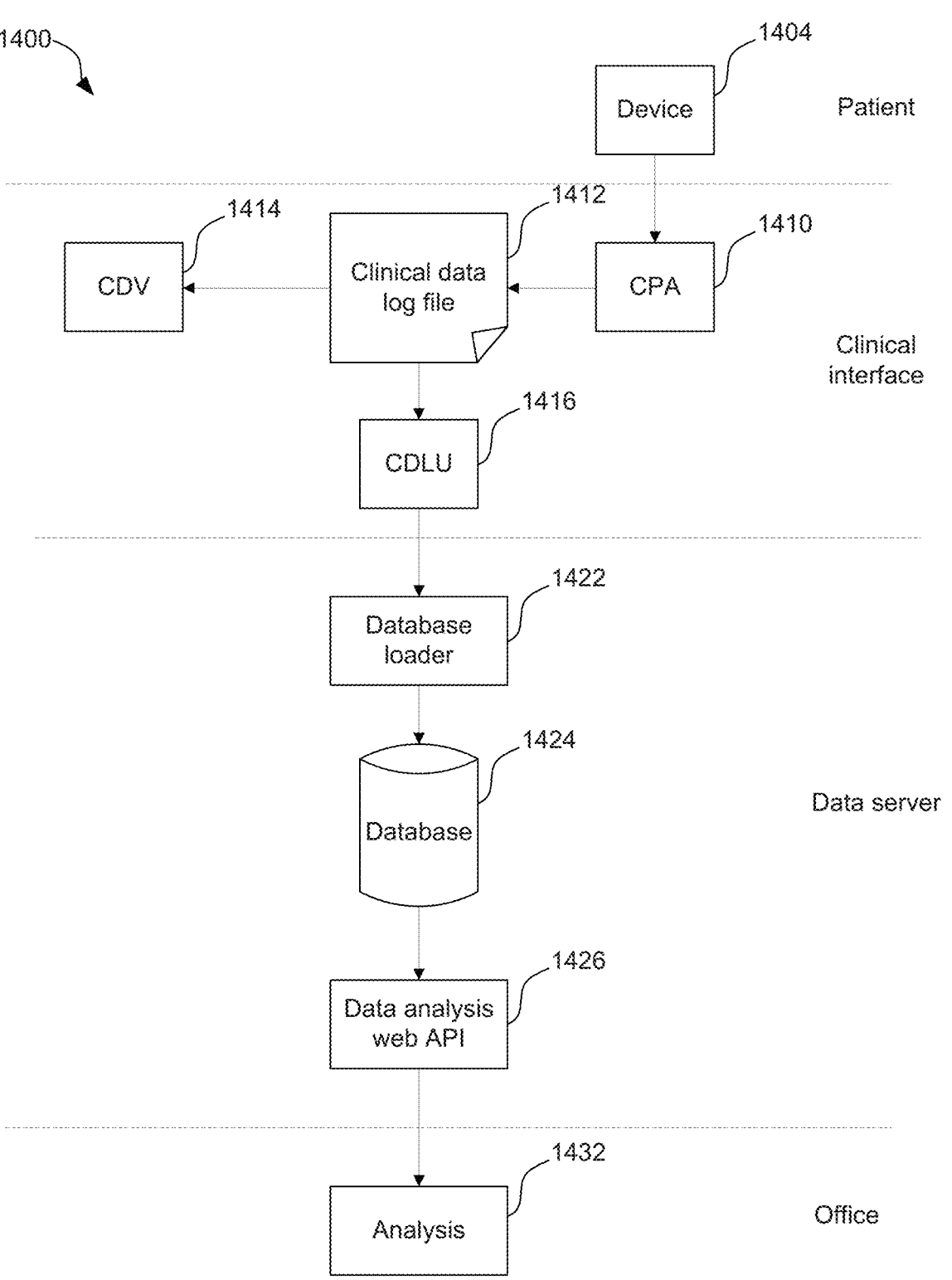
FIG. 14 is a block diagram illustrating the data flow of a neuromodulation therapy system, in accordance with an embodiment.

FIG. 14 is a block diagram illustrating the data flow 1400 of a neuromodulation therapy system such as the system 1300 of FIG. 13, in accordance with an embodiment.

Neuromodulation device 1404, once implanted within a patient, applies stimuli over a potentially long period such as weeks or months and records neural responses, clinical settings, paraesthesia target level, and other operational parameters, discussed further below. Neuromodulation device 1404 may comprise a Closed-Loop Stimulator (CLS), in that the recorded neural responses are used in a feedback arrangement to control clinical settings on a continuous or ongoing basis. To effect suitable SCS therapy, neuromodulation device 1404 may deliver tens, hundreds or even thousands of stimuli per second, for many hours each day. The feedback loop may operate for most or all of this time, by obtaining neural response recordings following every stimulus, or at least obtaining such recordings regularly. Each recording generates a feedback variable such as a measure of the amplitude of the evoked neural response, which in turn results in the feedback loop changing at least one stimulus parameter for a following stimulus. Neuromodulation device 1404 thus produces such data at a rate of tens or hundreds of Hz, or even kHz, and over the course of hours or days this process results in large amounts of clinical data.

When brought in reception range of a receiver, neuromodulation device 1404 transmits data, e.g. via telemetry module 114, to a clinical programming application (CPA) 1410 installed on a clinical interface. In one implementation, the clinical interface is the CI 1340 of FIG. 13. The data can be grouped into two main categories: (1) data collected in real-time during a programming session; and (2) data downloaded from a stimulator after a period of non-clinical use by a patient. CPA 1410 collects and compiles the data into a clinical data log file 1412.

Clinical data transmitted by the neuromodulation device 1404 may be compressed by use of a data compression technique before transmission by telemetry module 114 and/or before storage into the memory 118 to enable storage by neuromodulation device 1404 of higher resolution data. This higher resolution allows neuromodulation device 1404 to provide more data for post-analysis and more detailed data mining for events during use. Alternatively, compression enables faster transmission of standard-resolution clinical data.

The clinical data log file 1412 is manipulated, analysed, and efficiently presented by a clinical data viewer (CDV) 1414 for field diagnosis by a clinician, field clinical engineer (FCE) or the like. CDV 1414 is a software application installed on the Clinical Interface (CI). In one implementation, CDV 1414 opens one clinical data log file 1412 at a time. CDV 1414 is intended to be used in the field to diagnose patient issues and optimise therapy for the patient. CDV 1414 may be configured to provide the user or clinician with a summary of neuromodulation device usage, therapy output, and errors, in a simple single-view page immediately after log files are compiled upon device connection.

Clinical Data Uploader 1416 is an application that runs in the background on the CI, that uploads files generated by the CPA 1410, such as the clinical data log file 1412, to a data server. Database loader 1422 is a service which runs on the data server and monitors the patient data folder for new files. When Clinical Data Log files are uploaded by Clinical Data Uploader 1416, database loader 1422 extracts the data from the file and loads the extracted data to Database 1424.

The data server further contains a data analysis web API 1426 which provides data for third-party analysis such as by the analysis module 1432, located remotely from the data server. The ability to obtain, store, download and analyse large amounts of neuromodulation data means that the present technology can: improve patient outcomes in difficult conditions; enable faster, more cost effective and more accurate troubleshooting and patient status; and enable the gathering of statistics across patient populations for later analysis, with a view to diagnosing aetiologies and predicting patient outcomes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

References herein to estimation, determination, comparison and the like are to be understood as referring to an automated process carried out on data by a processor operating to execute a predefined procedure suitable to effect the described estimation, determination and/or comparison step(s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

| Label list | |
| --- | --- |
| stimulator | 100 |
| patient | 108 |
| electronics module | 110 |
| battery | 112 |
| telemetry module | 114 |
| controller | 116 |
| memory | 118 |
| clinical data | 120 |
| clinical settings | 121 |
| control programs | 122 |
| pulse generator | 124 |
| electrode selection module | 126 |
| measurement circuitry | 128 |
| ground | 130 |
| electrode array | 150 |
| biphasic stimulus pulse | 160 |
| neural response | 170 |
| nerve | 180 |
| transcutaneous communications channel | 190 |
| external computing device | 192 |
| closed-loop neural stimulation (CLNS) system | 300 |
| clinical settings controller (clinical settings) | 302 |
| target ECAP controller | 304 |
| dashed box representation of spinal cord | 308 |
| evocation of a neural response | 309 |
| feedback controller | 310 |
| evocation of an artefact signal | 311 |
| stimulator | 312 |
| summing element | 313 |
| measurement circuitry | 318 |
| ECAP detector | 320 |
| comparator | 324 |
| sensed signal r | 330 |
| neural response intensity d | 332 |
| gain element | 336 |
| integrator | 338 |
| ECAP | 400 |
| activation plot | 502 |
| ECAP threshold | 504 |
| discomfort threshold | 508 |
| perception threshold | 510 |
| therapeutic range | 512 |
| target ECAP amplitude | 520 |
| activation plot | 602 |
| activation plot | 604 |
| activation plot | 606 |
| ECAP threshold for activation plot 602 | 608 |
| ECAP threshold for activation plot 604 | 610 |
| ECAP threshold for activation plot 606 | 612 |
| ECAP target | 620 |
| activation plot | 702 |
| stimulus current level | 704 |
| sub-ECAP-threshold (sub-threshold) region | 708 |
| supra-ECAP-threshold (supra-threshold) region | 710 |
| supra-ECAP-threshold region | 720 |
| supra-perception-threshold region | 730 |
| supra-discomfort-threshold region | 740 |
| current source | 902 |
| stimulus electrode | 904 |
| feedback sense electrode | 906 |
| compensation electrode | 908 |
| measurement electrode | 910 |
| feedback amplifier | 912 |
| ground | 914 |
| neural response measurement circuitry | 916 |
| stimulation data set | 1030 |
| stimulation data set | 1040 |
| neuromodulation system | 1300 |
| neuromodulation device | 1310 |
| remote controller | 1320 |
| Clinical System Transceiver (CST) | 1330 |
| Clinical Interface (CI) | 1340 |
| charger | 1350 |
| data flow | 1400 |
| neuromodulation device | 1404 |
| clinical programming application (CPA) | 1410 |
| clinical data log file | 1412 |

| -continued | |
| --- | --- |
| Label list | |
| clinical data viewer (CDV) | 1414 |
| Clinical Data Uploader | 1416 |
| Database loader | 1422 |
| Database | 1424 |
| API | 1426 |
| analysis module | 1432 |

The invention claimed is:

1. A method of controlling delivery of neural stimuli, the delivery being defined by an artefact mitigation status, the method comprising:

generating a first neural stimulus for delivery to neural tissue;

sensing a first sensed signal subsequent to the first neural stimulus;

generating a second neural stimulus for delivery to the neural tissue;

sensing a second sensed signal subsequent to the second neural stimulus;

determining an artefact mitigation measure (AMM) effect level based on the first sensed signal and the second sensed signal, the AMM effect level comprising a measure of an effect of an artefact mitigation measure on an artefact component of the first sensed signal or the second sensed signal; and setting, in response to comparing the AMM effect level with an AMM effect threshold, the artefact mitigation status of a third neural stimulus to active.

2. The method of claim 1, further comprising generating the third neural stimulus for delivery to the neural tissue according to the artefact mitigation status.

3. The method of claim 1, wherein the artefact mitigation status of the first neural stimulus is active, and the artefact mitigation status of the second neural stimulus is inactive.

4. The method of claim 1, wherein the first neural stimulus is generated at supra-threshold intensity and the second neural stimulus is generated at supra-threshold intensity.

5. The method of claim 1, further comprising repeating generating the first neural stimulus and sensing the first sensed signal to generate a plurality of first sensed signals before determining the AMM effect level.

6. The method of claim 1, further comprising repeating generating the second neural stimulus and sensing the second sensed signal to generate a plurality of second sensed signals before determining the AMM effect level.

7. The method of claim 1, wherein determining the AMM effect level comprises:

determining an artefact-to-evoked compound action potential (ECAP) ratio of the first sensed signal;

determining an artefact-to-ECAP ratio of the second sensed signal; and comparing the artefact-to-ECAP ratio of the first sensed signal to the artefact-to-ECAP ratio of the second sensed signal.

8. The method of claim 7, wherein determining the artefact-to-ECAP ratio of the first sensed signal comprises applying basis element signal separation to the first sensed signal.

9. The method of claim 7, wherein determining the artefact-to-ECAP ratio of the first sensed signal comprises fitting a growth curve model to the first sensed signal.

10. The method of claim 7, wherein determining the artefact-to-ECAP ratio of the first sensed signal comprises fitting an artefact-aware growth curve model to the first sensed signal.

11. The method of claim 1, wherein the first neural stimulus is generated at sub-threshold intensity, and the second neural stimulus is generated at sub-threshold intensity.

12. The method of claim 1, wherein the first neural stimulus is defined by a first stimulus electrode configuration defining a first subset of stimulus electrodes from a plurality of stimulus electrodes of an electrode array, and wherein the second neural stimulus is defined by a second stimulus electrode configuration defining a second subset of stimulus electrodes from the plurality of stimulus electrodes of the electrode array, the first subset differing from the second subset.

13. The method of claim 1, further comprising, in response to the artefact mitigation status being active, controlling an electrical condition of the neural tissue.

14. The method of claim 13, wherein controlling an electrical condition of the neural tissue comprises:

providing a plurality of electrodes including at least one nominal feedback sense electrode and at least one nominal compensation electrode, the electrodes being positioned proximate to the neural tissue and being in electrical contact with the neural tissue;

connecting a feedback signal from the feedback sense electrode to an input of a feedback amplifier, and referencing the amplifier to a desired electrical value; and connecting an output of the feedback amplifier to the compensation electrode such that the feedback amplifier drives the neural tissue via the compensation electrode in a feedback arrangement which seeks to drive the feedback signal to the desired electrical value.

15. The method of claim 14, wherein the desired electrical value is electrical ground referenced to a patient ground electrode distant from the feedback sense electrode.

16. An implantable device for controllably delivering neural stimuli, the delivery being defined by an artefact mitigation activation status, the device comprising:

a stimulus source configured to generate neural stimuli to be delivered via one or more stimulus electrodes of an electrode array to neural tissue;

measurement circuitry configured to sense signals of the neural tissue via one or more measurement electrodes of the electrode array subsequent to respective neural stimuli; and a controller configured to:

control the stimulus source to generate a first neural stimulus for delivery to the neural tissue;

sense, by the measurement circuitry, a first sensed signal of the neural tissue, subsequent to the first neural stimulus;

control the stimulus source to generate a second neural stimulus for delivery to the neural tissue;

sense, by the measurement circuitry, a second sensed signal of the neural tissue, subsequent to the second neural stimulus;

determine an AMM effect level based on the first sensed signal and the second sensed signal, the AMM effect level comprising a measure of an effect of an artefact mitigation measure on an artefact component of the first sensed signal or the second sensed signal; and set, in response to comparing the AMM effect level with an AMM effect threshold, the artefact mitigation status of a third neural stimulus to active.

17. The device of claim 16, wherein the controller is further configured to control the stimulus source to generate the third neural stimulus for delivery to the neural tissue according to the artefact mitigation status.

18. The device of claim 16, further comprising the electrode array, the electrode array comprising a plurality of electrodes including the one or more stimulus electrodes and the one or more measurement electrodes.

19. The device of claim 16, wherein the artefact mitigation status is defined by an artefact mitigation configuration setting of the implantable device.

20. The device of claim 16, wherein the controller is configured to, in response to the AMM effect level exceeding the AMM effect threshold, set the artefact mitigation status to active.

21. A neuromodulation system comprising:

an implantable device for controllably delivering neural stimuli, the delivery being defined by an artefact mitigation activation status, the device comprising:

a stimulus source configured to generate neural stimuli to be delivered via one or more stimulus electrodes of an electrode array to neural tissue;

measurement circuitry configured to sense signals of the neural tissue via one or more measurement electrodes of the electrode array subsequent to respective neural stimuli; and a controller configured to control the stimulus source to generate the neural stimuli; and a processor configured to:

instruct the controller to control the stimulus source to generate a first neural stimulus for delivery to the neural tissue;

instruct the measurement circuitry to sense a first sensed signal of the neural tissue, subsequent to the first neural stimulus;

instruct the controller to control the stimulus source to generate a second neural stimulus for delivery to the neural tissue; and instruct the measurement circuitry to sense a second sensed signal of the neural tissue, subsequent to the second neural stimulus;

determine an AMM effect level based on the first sensed signal and the second sensed signal, the AMM effect level comprising a measure of an effect of an artefact mitigation measure on an artefact component of the first sensed signal or the second sensed signal; and set, in response to comparing the AMM effect level with an AMM effect threshold, the artefact mitigation status to active.

22. The neuromodulation system of claim 21, further comprising the electrode array, the electrode array comprising a plurality of electrodes including the one or more stimulus electrodes and the one or more measurement electrodes.

23. The neuromodulation system of claim 21, wherein the artefact mitigation status is defined by an artefact mitigation configuration setting of the implantable device.

24. The neuromodulation system of claim 21, wherein the processor is configured to, in response to the AMM effect level exceeding the AMM effect threshold, set the artefact mitigation status to active.

25. The neuromodulation system of claim 21, wherein the processor is part of the implantable device.

26. The neuromodulation system of claim 21, further comprising an external computing device in communication with the implantable device.

27. The neuromodulation system of claim 26, wherein the processor is part of the external computing device.

28. A method of controlling delivery of neural stimuli, the delivery being defined by an artefact mitigation status, the method comprising:

determining an impedance of a recording electrode;

determining an impedance of a reference electrode;

determining an expected artefact level based on the impedance of the recording electrode and the impedance of the reference electrode;

setting, in response to comparing the expected artefact level with a threshold artefact level, the artefact mitigation status of neural stimuli to active; and generating the neural stimulus for delivery to neural tissue according to the artefact mitigation status.

29. The method of claim 28, wherein the expected artefact level comprises an expected artefact magnitude.

30. The method of claim 29, wherein the threshold artefact level comprises a threshold artefact magnitude.

31. The method of claim 28, wherein the expected artefact level comprises an impedance difference between the impedance of the recording electrode and the impedance of the reference electrode.

32. The method of claim 31, wherein the threshold artefact level comprises a threshold impedance difference.

33. The method of claim 28, wherein determining the expected artefact level is further based on an input capacitance of an amplifier to which the recording electrode and the reference electrode are connected.

34. An implantable device for controllably delivering neural stimuli, the delivery being defined by an artefact mitigation activation status, the device comprising:

a stimulus source configured to generate neural stimuli to be delivered via one or more stimulus electrodes of an electrode array to a neural tissue;

measurement circuitry configured to sense signals of the neural tissue via one or more measurement electrodes of the electrode array subsequent to respective neural stimuli; and a controller configured to:

determine an impedance of a recording electrode of the one or more measurement electrodes;

determine an impedance of a reference electrode of the one or more measurement electrodes;

determine an expected artefact level based on the impedance of the recording electrode and the impedance of the reference electrode; and set, in response to comparing the expected artefact level with a threshold artefact level, the artefact mitigation status of neural stimuli to active.

35. The device of claim 34, wherein the controller is further configured to control the stimulus source to generate a neural stimulus for delivery to the neural tissue according to the artefact mitigation status.

36. A neuromodulation system comprising:

an implantable device for controllably delivering neural stimuli, the delivery being defined by an artefact mitigation activation status, the device comprising:

a stimulus source configured to generate neural stimuli to be delivered via one or more stimulus electrodes of an electrode array to neural tissue;

measurement circuitry configured to sense signals of the neural tissue via one or more measurement electrodes of the electrode array subsequent to respective neural stimuli; and a controller configured to control the stimulus source to generate the neural stimuli; and a processor configured to:

determine an impedance of a recording electrode of the one or more measurement electrodes;

determine an impedance of a reference electrode of the one or more measurement electrodes;

determine an expected artefact level based on the impedance of the recording electrode and the impedance of the reference electrode; and set, in response to comparing the expected artefact level with a threshold artefact level, the artefact mitigation status of neural stimuli to active.

37. The neuromodulation system of claim 36, wherein the controller is further configured to control the stimulus source to generate a neural stimulus for delivery to the neural tissue according to the artefact mitigation status.

38. The neuromodulation system of claim 36, wherein the processor is part of the implantable device.

39. The neuromodulation system of claim 36, further comprising an external computing device in communication with the implantable device.

40. The neuromodulation system of claim 39, wherein the processor is part of the external computing device.

* * * * *